United States Patent
Leuwer et al.

(10) Patent No.: US 8,507,724 B2
(45) Date of Patent: Aug. 13, 2013

(54) COMPOUNDS FOR USE IN THE TREATMENT OF PAIN

(75) Inventors: Martin Leuwer, Liverpool (GB); Paul O'Neill, Liverpool (GB); Neil Berry, Liverpool (GB); Gertrud Haeseler, Hannover (GB)

(73) Assignee: The University of Dundee, Dundee, Scotland (GB)

( * ) Notice: Subject to any disclaimer, the term of this patent is extended or adjusted under 35 U.S.C. 154(b) by 0 days.

(21) Appl. No.: 13/133,569

(22) PCT Filed: Dec. 9, 2009

(86) PCT No.: PCT/GB2009/002850
§ 371 (c)(1),
(2), (4) Date: Sep. 14, 2011

(87) PCT Pub. No.: WO2010/067069
PCT Pub. Date: Jun. 17, 2010

(65) Prior Publication Data
US 2012/0029235 A1 Feb. 2, 2012

(30) Foreign Application Priority Data
Dec. 10, 2008 (GB) .................................. 0822486.7

(51) Int. Cl.
C07C 233/00 (2006.01)
C07C 235/00 (2006.01)
C07C 237/00 (2006.01)
C07C 239/00 (2006.01)
C07C 39/12 (2006.01)
C07C 43/20 (2006.01)

(52) U.S. Cl.
USPC ............ 564/171; 568/642; 568/746; 568/747

(58) Field of Classification Search
None
See application file for complete search history.

(56) References Cited

FOREIGN PATENT DOCUMENTS

| JP | 7089898 A | | 4/1995 |
|---|---|---|---|
| JP | 2002093609 | * | 3/2002 |
| JP | 3498853 | * | 12/2003 |
| JP | 3498853 B2 | | 2/2004 |
| WO | WO-99/58521 A1 | | 11/1999 |
| WO | WO-99/61435 A1 | | 12/1999 |
| WO | WO-2007/071967 A2 | | 6/2007 |

OTHER PUBLICATIONS

Nishide et al. Hyperbranched poly(phenylenevinylene) bearing pendant phenoxys for a high-spin alignment. J. Mater. Chem., 2002, 12, 3578-3584.*
JP2002093609. Translated on Jun. 15, 2012.*
JP3498853. English language translation. Translated on Oct. 11, 2012.*
RN 168196-71-2, RN 168196-82-5, Entered STN: Sep. 29, 1995.*
Ito et al. A medium-term rat liver bioassay for rapid in vivo detection of carcinogenic potential of chemicals. Cancer Sci. 2003; 94: 3-8.*
International Search Report mailed on Jun. 1, 2010, for PCT Application No. PCT/GB2009/002850, filed on Dec. 9, 2009, 4 pages.
Trapani, G. et al. (Jan. 1, 1998, e-published Apr. 28, 1998). "Propofol Analogues, Synthesis, Relationships Between Structure and Affinity at $GABA_A$ Receptor in Rat Brain, and Differential Electrophysiological Profile at Recombinant Human $GABA_A$ Receptors," *Journal of Medicinal Chemistry* 41(11):1846-1854.

* cited by examiner

*Primary Examiner* — Brandon Fetterolf
*Assistant Examiner* — Anna Pagonakis
(74) *Attorney, Agent, or Firm* — Morrison & Foerster LLP

(57) ABSTRACT

The present invention concerns compounds derived from the anaethetic propofol. The compounds may be useful in the treatment of pain, particularly, but not exclusively, chronic pain and central pain sensitisation.

22 Claims, 4 Drawing Sheets

COMPOUNDS FOR USE IN THE TREATMENT OF PAIN

CROSS REFERENCE TO RELATED APPLICATIONS

Figure 1:
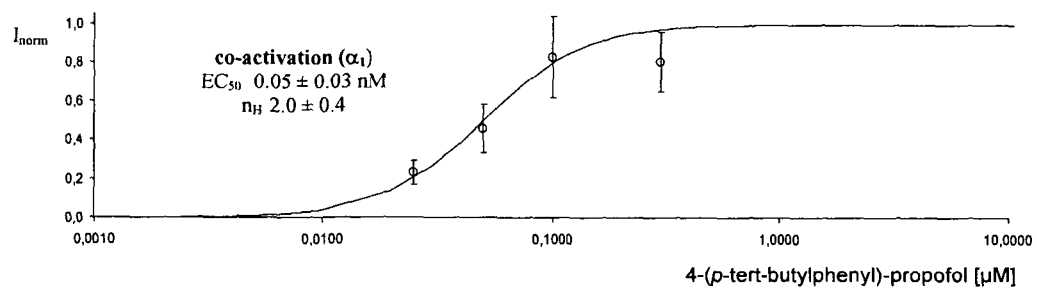

This patent application is a National Phase application under 35 U.S.C. §371 of International Application No. PCT/GB2009/002850, filed Dec. 9, 2009, which claims the benefit of United Kingdom Application No. 0822486.7, filed Dec. 10, 2008, the disclosures of which are incorporated herein by reference in their entirety.

The present invention relates to compounds derived from the anaesthetic propofol. The compounds are useful in the treatment of pain, particularly, but not exclusively, chronic pain and central pain sensitisation.

Effective safe pain control is regarded worldwide as a high priority clinical need. However the majority of developments in this field have failed to deliver high efficacy products free of undesirable side effects and safety issues. The opiates probably remain as the most effective treatment available and the ultimate goal is to deliver a pain control agent with the efficacy of the opiates but without the sedation, dependance, gastric damage and general tolerability problems.

It has been postulated that phenol derivatives may have a number of neuromodulatory effects. However the only phenol derivative in widespread clinical use is the anaesthetic propofol (2,6-di-isopropylphenol).

Key features of anaesthesia are loss of consciousness, immobility in the presence of painful stimuli and absence of recall. Anaesthetics, such as propofol, are understood to mediate their anaesthetic effect by activating γ-aminobutyric acid ($GABA_A$) receptors in the Central Nervous System (CNS).

In contrast, analgesia is defined as the absence of pain. Among other peripheral and/or central nervous mechanisms, analgesia can arise as a result of enhanced inhibitory synaptic transmission within the dorsal horn of the spinal chord. It is understood that inhibitory postsynaptic transmission in the spinal chord involves mainly glycine receptors. Accordingly the glycine receptor family represents a target site for therapeutic agents aiming at inhibiting pain.

Both, $GABA_A$ and glycine receptors belong to the ligand-gated ion channel superfamily. They have a common structure in which five subunits form an ion channel. α and β subunits assemble into a pentameric receptor with a proposed in vivo stochiometry of 3α: 2β. Glycine receptors, like $GABA_A$ receptors, inhibit neuronal firing by opening chloride channels following agonist binding. Glycine receptors are mainly found in lower areas of the central nervous system and are involved in the control of motor rhythm generation, the coordination of spinal nociceptive reflex responses and the processing of sensory signals.

There exists a need to develop new and improved analgesics. Despite that fact that glycine receptors represent a good target for identifying such analgesics, there are no existing analgesics that target these receptors. The inventors therefore decided to address this issue and exploited their knowledge of the pathophysiological mechanisms underlying anaesthesia and analgesia with a view to identifying new and improved drugs for controlling pain.

Chronic pain is very different from acute pain. Acute pain can be considered as a useful early warning system informing us about noxious stimuli and thereby helping us to escape and prevent damage. Chronic pain, in contrast, is a disease in its own right. Experts regard it as a dys-equilibrium syndrome, where inhibitory neuronal activity which under normal circumstances suppresses the processing of pain is markedly reduced. Treatment of chronic inflammatory or neuropathic pain is still difficult, and there is currently no single treatment that works for all conditions.

Increased neuronal excitability seen in chronic pain involves a loss of inhibition mediated by GABA- and/or glycinergic neurons in the superficial dorsal horn of the spinal cord that control the relay of nociceptive signals from the periphery to higher areas of the central nervous system. In the adult dorsal horn, the contribution of glycine to fast inhibitory postsynaptic transmission dominates. Glycine receptors are mainly found in lower areas of the central nervous system and are involved in the control of motor rhythm generation, the coordination of spinal nociceptive reflex responses and the processing of sensory signals. Their role in modulating ascending nociceptive pathways and pain makes them a potentially interesting target site for analgesic and spasmolytic agents. Microinjection of the glycine receptor agonist taurine into the anterior cingulate cortex—associated with the affective component of pain—relieves neuropathic pain, an effect that could be antagonized by the selective glycine receptor antagonist strychnine. There are four α-subunits and one β-subunit for the strychnine-sensitive glycine receptor, the α1-subunit is widely expressed in the adult spinal cord and brain stem, but also in higher centres of the brain involved in sensory processing. The glycine receptor α3-subunit has been identified as a target site underlying central inflammatory pain sensitization due to $PGE_2$-induced receptor phosphorylation. α3-subunit knock-out mice do not develop inflammatory pain with otherwise normal response to acute pain. This phenomenon may be explained by the fact that α1 containing glycine receptor subunits which probably compensate for the lack in α3 do not possess the protein kinase A (PKA) phosphorylation site involved in the $PGE_2$ signal transduction. Furthermore, phosphorylation of the α3 subunit is not necessarily involved in neuropathic pain. Based on this understanding, a need has been identified by the inventors for the development of drugs that target the predominant adult glycine receptor isoform containing the α1 subunit. Given the physiological role of glycine receptors and their relatively restricted expression (mainly in the spinal cord and lower brain areas), a selective glycine modulator should be of great interest therapeutically to increase inhibition at the level of the spinal cord dorsal horn.

According to a first aspect of the present invention there is provided a compound of general formula (IA)

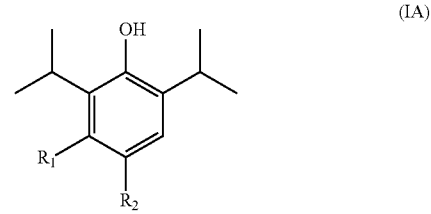

wherein $R_1$ is

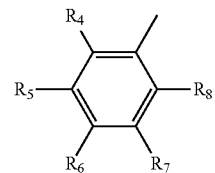

wherein $R_4$, $R_5$, $R_6$, $R_7$ and $R_8$ are each separately selected from the group consisting of hydrogen, halogen, substituted or unsubstituted alkyl, substituted or unsubstituted alkoxy, substituted or unsubstituted amine, substituted or unsubstituted amide, substituted or unsubstituted aryl and substituted or unsubstituted heteroaryl; and/or wherein $R_2$ is

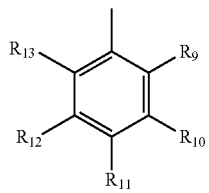

wherein $R_9$, $R_{10}$, $R_{11}$, $R_{12}$ and $R_{13}$ are each separately selected from the group consisting of hydrogen, halogen, substituted or unsubstituted alkyl, substituted or unsubstituted alkoxy, substituted or unsubstituted amine, substituted or unsubstituted amide, substituted or unsubstituted aryl and substituted or unsubstituted heteroaryl.

The present invention still further provides compounds of general formula (I) for use in the treatment of pain

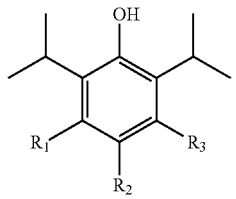

(I)

wherein at least one of $R_1$, $R_2$ and $R_3$ is or comprises a substituted or unsubstituted aryl or heteroaryl group.

Very recently, an alternative approach to increase inhibition in the spinal cord via targeting spinal $GABA_A$ receptors has been published. Due to their ubiquitous expression all over the central nervous system, the $GABA_A$ receptors are a therapeutic target for structurally diverse sedative-anaesthetic and anxiolytic drugs. Thus, analgesic effects of GABA-modulatory agents like benzodiazepines that are present upon spinal injection are overridden by their central nervous effects upon systemic administration. It has previously been shown that $GABA_A$ receptors that contain α2 and/or α3 $GABA_A$ receptor subunits are involved in the antinociceptive actions of benzodiazepines at the spinal level, suggesting the development of subtype-selective GABAergic drugs for the treatment of chronic pain. In contrast to this latest work, the inventor's approach is to selectively target glycine receptors rather than $GABA_A$ receptors to develop compounds according to general formula I and IA to treat chronic pain by enhancing/restoring inhibition at the level of the spinal cord while avoiding sedation and dependence associated with the stimulation of $GABA_A$ receptors in higher brain areas. The inventor's approach targets the glycine receptor α1-subunit, which is known to be positively modulated by anaesthetics, alcohols and cannabinoids, but for the first time the compounds according to the present invention target the intended receptor family with high affinity, rather than being relatively unspecific as with all known compounds which target other receptor families (e.g. the $GABA_A$ receptor in the case of anaesthetics) with higher affinity. The present invention further provides a compound of general formula I, IA and preferred embodiments thereof for use in the treatment of pain.

According to further related aspects of the present invention there are provided methods for the production of compounds of general formulae (X) and (XIII) by the reaction of a compound of the general formula (XI) or (XIV) with a compound of general formula (XII) or (XV) respectively as set out below:

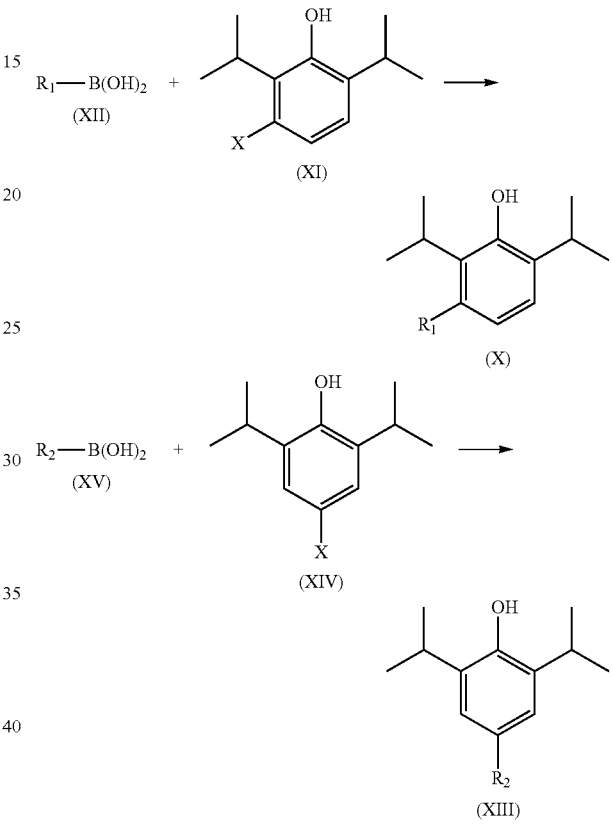

wherein each of $R_1$ and $R_2$ is or comprises a substituted or unsubstituted aryl or heteroaryl group and X is a halogen atom selected from the group consisting of fluorine, chlorine and bromine.

A further aspect of the present invention provides a pharmaceutical composition comprising a therapeutically effective amount of a compound according to the first aspect of the present invention, or a compound of general formula I or IA, and a pharmaceutically acceptable vehicle.

A yet further aspect of the present invention provides a pharmaceutical composition for the treatment of pain comprising an effective amount of a compound according to the first aspect of the present invention, or a compound of general formula I or IA, and a pharmaceutically acceptable excipient.

Another aspect provides a method of treating or reducing pain in a subject in need of such treatment comprising administering to said subject a therapeutically effective amount of a compound as defined in the first aspect of the present invention, or a compound of general formula I or IA.

Still further aspects provide a medicament comprising the compound defined by the first aspect of the present invention, or a compound of general formula I or IA; and a compound according to the first aspect of the present invention, or a compound of general formula I or IA, as a medicament for use in the treatment of pain.

A yet further aspect of the present invention provides a compound according to the first aspect of the present invention, or a compound of general formula I or IA, for use in the manufacture of a medicament for the treatment of pain.

Another aspect provides the use of a compound according to the first aspect of the present invention, or a compound of general formula I or IA, for the treatment of pain.

A second aspect of the present invention provides a pharmaceutical composition for the treatment of pain comprising an effective amount of a compound having the formula (VIII)

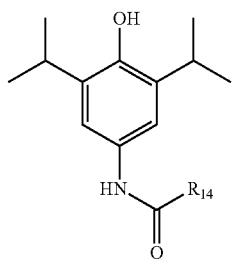

(VIII)

wherein $R_{14}$ is a halo-alkyl group; and a pharmaceutically acceptable excipient.

The present invention further provides a compound for use in the treatment of pain having the formula (VIII).

A further aspect of the present invention provides a pharmaceutical composition for the treatment of pain comprising an effective amount of a compound according to the second aspect of the present invention, or a compound of general formula VIII or IX, and a pharmaceutically acceptable excipient.

Another aspect provides a method of treating or reducing pain in a subject in need of such treatment comprising administering to said subject a therapeutically effective amount of a compound as defined in the second aspect of the present invention, or a compound of general formula VIII or IX.

A still further aspect provides a medicament for use in the treatment of pain comprising the compound defined by the second aspect of the present invention, or a compound of general formula VIII or IX.

A yet further aspect of the present invention provides a compound according to the second aspect of the present invention, or a compound of general formula VIII or IX for use in the manufacture of a medicament for the treatment of pain.

Another aspect provides the use of a compound according to the second aspect of the present invention, or a compound of general formula VIII or IX, for the treatment of pain.

The inventors recognized that a loss of inhibitory synaptic transmission within the dorsal horn of the spinal cord plays a key role in the development of chronic pain following inflammation or nerve injury. Furthermore they recognized that inhibitory postsynaptic transmission in the spinal cord involves mainly glycine. This lead them to realise that the strychnine-sensitive glycine receptor family represents a target site for therapeutic agents aiming at inhibiting pain sensitization. This realization was based upon work conducted by Ahmadi et al. (Nature Neuroscience (2001) Vol. 5 No. 1 p 34-40).

The inventors proceeded to test their hypothesis by studying phenol derivatives with a halogen in the para position to the hydroxyl group and one or two methyl groups in the ortho or meta positions. Their results were published by Haeseler et al. (British Journal of Pharmacology (2005) 145, p 916-925) and established that halogenation improved co-activation or activation of glycine receptors. However these initial results appeared to demonstrate that the number or position of the methyl groups on the phenol ring did not significantly effect the $EC_{50}$ for co-activation of the glycine receptors.

The inventors therefore developed improved analgesics that specifically target glycine receptors and to their surprise they discovered that propofol analogues incorporating ortho- or meta-alkyl groups comprising two or more carbon atoms and para-halo, amino or amido groups exhibited unexpected potency as co-activators of glycine receptors. This work is the subject of the applicant's International patent application WO2007/071967.

The compounds described in the Examples exhibited half-maximum potentiating effects in the low nanomolar range. This represents orders of magnitude lower concentrations than for propofol. Furthermore compounds according to the present invention were significantly more potent than the p-methyl and p-halo derivatives described in earlier published work. This is a great advantage because it means that compounds according to the present invention will be ideal analgesics and will have no or negligible effects on consciousness (i.e. anaesthetic effects).

With regard to compounds of general formula I and IA it is preferred that said aryl or heteroaryl group is a monocyclic aromatic ring or a polycyclic aromatic ring. Said aryl or heteroaryl group may be unsubstituted, or may be substituted with one or more substituents selected from the group consisting of halogen, substituted or unsubstituted alkyl, substituted or unsubstituted alkoxy, substituted or unsubstituted amine, substituted or unsubstituted amide, substituted or unsubstituted aryl and substituted or unsubstituted heteroaryl. One of said one or more substituents may be provided at the ortho, meta and/or para position.

In a first preferred embodiment $R_1$ is a substituted or unsubstituted aryl or heteroaryl group and at least one of $R_2$ and $R_3$ is a hydrogen atom. A preferred compound has the general formula (II)

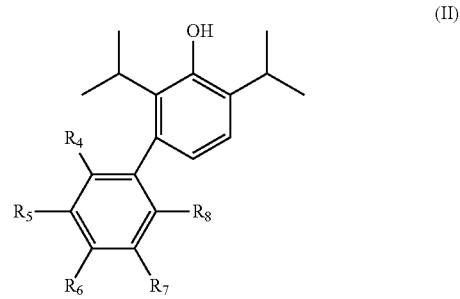

(II)

wherein $R_4$, $R_5$, $R_6$, $R_7$ and $R_8$ are each separately selected from the group consisting of hydrogen, halogen, substituted or unsubstituted alkyl, substituted or unsubstituted alkoxy, substituted or unsubstituted amine, substituted or unsubstituted amide, substituted or unsubstituted aryl and substituted or unsubstituted heteroaryl.

At least one of $R_4$ and $R_8$ may be halogen or substituted or unsubstituted $C_{1-4}$ alkyl. The halogen is preferably fluorine or chlorine and the alkyl group is preferably methyl, ethyl, propyl or butyl. It is preferred that $R_8$ is selected from the group consisting of fluoro, chloro and trifluoromethyl, and $R_4$ is hydrogen.

At least one of $R_5$ and $R_7$ is preferably selected from the group consisting of hydrogen, halogen and substituted or unsubstituted alkyl. The halogen may be fluorine or chlorine and the alkyl may be a halo-substituted $C_{1-4}$ alkyl. Preferably $R_7$ is selected from the group consisting of fluoro, chloro, trifluoromethyl and trifluoromethoxyl, and $R_5$ is selected from the group consisting of hydrogen, fluoro, chloro and trifluoromethyl.

$R_6$ is preferably selected from the group consisting of hydrogen, halogen, substituted or unsubstituted alkyl, substituted or unsubstituted alkoxy, and substituted or unsubstituted phenyl. Said halogen may be fluorine or chlorine, said alkyl may be a halo-substituted $C_{1-4}$ alkyl and said alkoxy may be a halo-substituted $C_{1-4}$ alkoxy. Preferably $R_6$ is selected from the group consisting of —C(O)NH$_2$, fluoro, chloro and trifluoromethyl, trifluoromethoxyl.

In a second preferred embodiment $R_2$ is a substituted or unsubstituted aryl or heteroaryl group and at least one of $R_1$ and $R_3$ is a hydrogen atom. A preferred compound has the general formula (III)

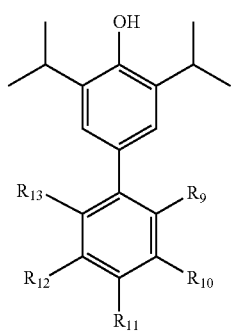

(III)

wherein $R_9$, $R_{10}$, $R_{11}$, $R_{12}$ and $R_{13}$ are each separately selected from the group consisting of hydrogen, halogen, substituted or unsubstituted alkyl, substituted or unsubstituted alkoxy, substituted or unsubstituted amine, substituted or unsubstituted amide, substituted or unsubstituted aryl and substituted or unsubstituted heteroaryl.

At least one of $R_9$ and $R_{13}$ is preferably halogen, such as fluorine or chlorine, or substituted or unsubstituted $C_{1-4}$ alkyl, for example methyl, ethyl, propyl or butyl. Preferably $R_9$ is selected from the group consisting of fluoro, chloro and trifluoromethyl, and $R_{13}$ is hydrogen.

Preferably at least one of $R_{10}$ and $R_{12}$ is selected from the group consisting of hydrogen, halogen and substituted or unsubstituted alkyl. Said halogen may be fluorine or chlorine and said alkyl may be a halo-substituted $C_{1-4}$ alkyl. It is preferred that $R_{10}$ is selected from the group consisting of fluoro, chloro, trifluoromethyl and trifluoromethoxyl, and $R_{12}$ is selected from the group consisting of hydrogen, fluoro, chloro and trifluoromethyl.

$R_{11}$ may be selected from the group consisting of hydrogen, halogen, substituted or unsubstituted alkyl, substituted or unsubstituted alkoxy, and substituted or unsubstituted phenyl. The halogen is preferably fluorine or chlorine, the alkyl is preferably a halo-substituted $C_{1-4}$ alkyl and the alkoxy is preferably a halo-substituted $C_{1-4}$ alkoxy. Preferably $R_6$ is selected from the group consisting of —C(O)NH$_2$, fluoro, chloro and trifluoromethyl, trifluoromethoxyl.

The present invention provides the following preferred compounds:

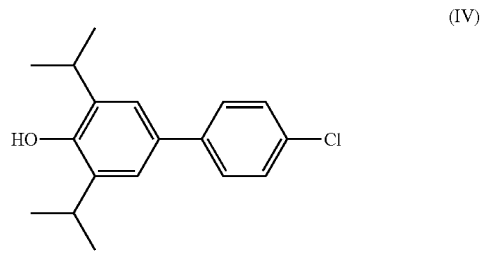

(IV)

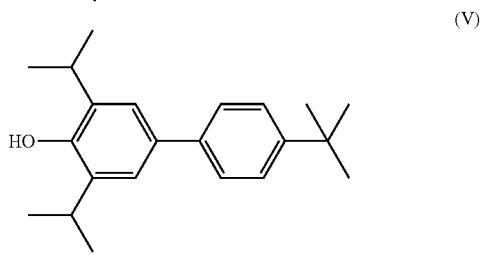

(V)

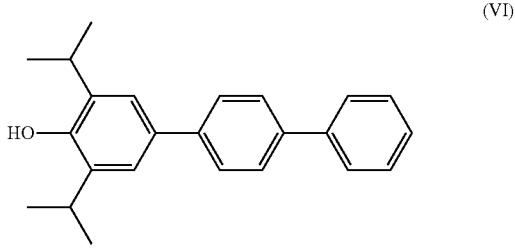

(VI)

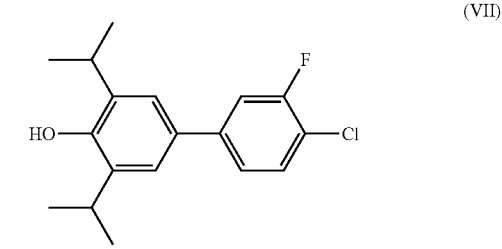

(VII)

The present invention further provides the above preferred compounds for use in the treatment of pain.

The second aspect of the present invention provides a pharmaceutical composition for the treatment of pain comprising an effective amount of a compound having the formula (VIII)

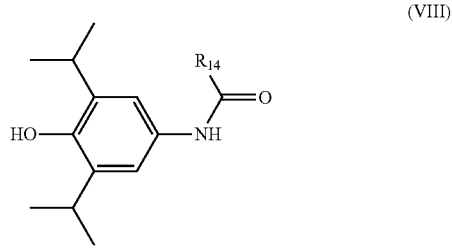

(VIII)

wherein $R_{14}$ is a halo-alkyl group; and a pharmaceutically acceptable excipient.

The present invention further provides a compound for use in the treatment of pain having the formula (VIII).

Preferably said alkyl group is a $C_{1-4}$alkyl group. $R_{14}$ may comprise two or more, preferably three, halo-substituents. Any appropriate halo-substituent may be selected, but it is preferred that the or at least one of said halo-substituents is fluorine.

The present invention further provides a pharmaceutical composition for the treatment of pain comprising an effective amount of a compound having the formula (IX)

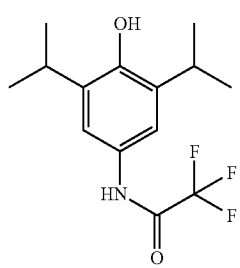

(XI)

The present invention further provides a compound for use in the treatment of pain having the formula (XI).

Still further preferred compounds according to the first aspect of the present invention can be selected from the following group:

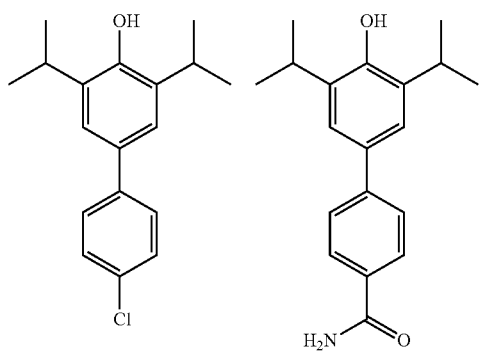

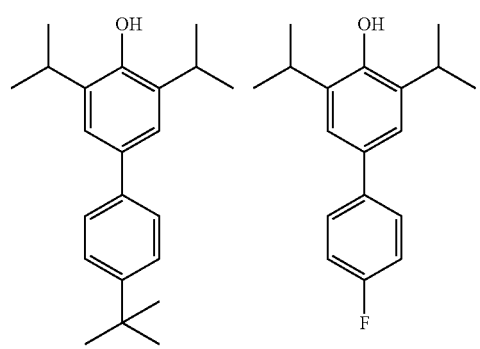

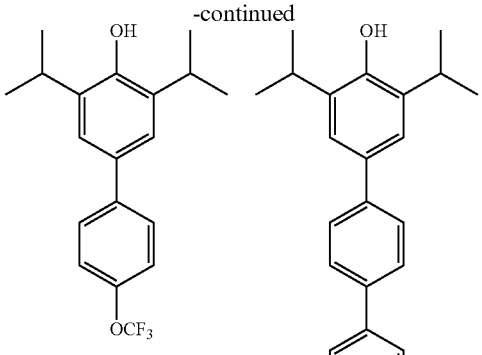

-continued

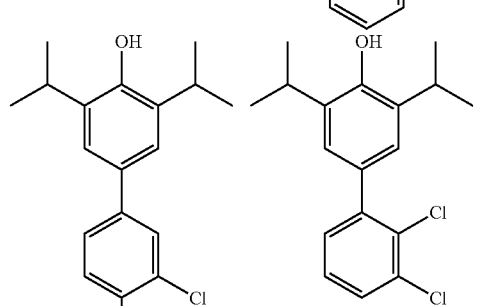

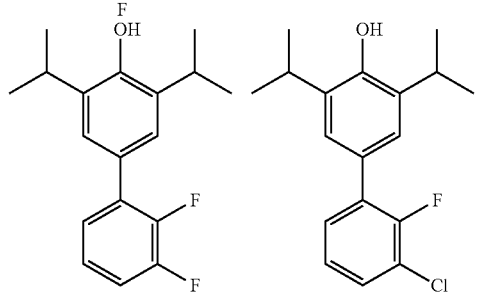

It is preferred that the compounds have selectivity for strychnine-sensitive glycine receptors over $GABA_A$ receptors. The compounds may have an $EC_{50}$ for co-activating glycine receptors at a lower concentration than their $EC_{50}$ at $GABA_A$ receptors. Preferably the compounds have an $EC_{50}$ for co-activating glycine receptors that is 10-fold lower than its $EC_{50}$ at $GABA_A$ receptors. It is more preferred that the compounds have an $EC_{50}$ for co-activating glycine receptors that is at least 100-fold lower than its $EC_{50}$ at $GABA_A$ receptors.

It is preferred that the compounds should also have an $EC_{50}$ for co-activating glycine receptors that is lower than that of propofol. For instance the compound may have an $EC_{50}$ for co-activating glycine receptors that is at least 10-fold lower or 100-fold lower than that of propofol. Most preferred compounds have an $EC_{50}$ for co-activating glycine receptors that is 1000-fold lower than that of propofol (measured on glycine receptors heterologously expressed in HEK293 cells).

Suitable methods for measuring $EC_{50}$ values for co-activating glycine receptors are disclosed in the Examples below.

The efficacy of the compounds is all the more surprising when the neurophysiology modulating anaesthesia in the CNS and analgesia in the PNS is considered. The inventors believe that compounds according to general formula I and IA act as positive allosteric modulators at strychnine-sensitive glycine receptors. These receptors are chloride channels that stabilise membrane potential by hyperpolarisation and constitute the predominant inhibitory principle at the spinal cord level. In contrast, the closely related $GABA_A$ receptor constitutes the predominant inhibitory principle in the CNS. A $GABA_A$ agonistic drug will, therefore, lead to an alteration or a loss of consciousness, whereas a compound according to the invention will ideally block pain at the peripheral level at concentrations that will not affect consciousness. The inventors believe compounds according to the invention have efficacy because they act as positive allosteric modulators at strychnine-sensitive glycine receptors and thereby block centripetal nerve signals at the dorsal root ganglionic level but have minimal or no effects at central $GABA_A$ receptors. It therefore follows, that a skilled person would choose an analgesic that was a glycine receptor agonist and which would have no $GABA_A$ agonistic effect at all. Consequently, propofol, which is the most potent $GABA_A$ agonist known, would be regarded by a skilled person as the least suitable compound to serve as a platform for developing analgesics. Furthermore a skilled person would also have reviewed the data published by Haeseler et al. (supra) and would have come to the view that the nature of the alkylation (methyl groups in the Haeseler paper) would not have been critical when developing a compound that is selective for glycine receptors over GABA receptors. The inventors therefore believe that there was a technical prejudice against investigating the analgesic properties of propofol derivatives. Thus, the extra-ordinary increase in glycine receptor co-activation that the inventors found with compounds according to the invention was not only surprising but would have been considered unlikely by the skilled artisan. In theory, any other phenol derivative with a lesser potency at the $GABA_A$ receptor level should, according to the state of the art, have been considered to be a more promising candidate.

In the methods for the production of compounds of general formulae (X) and (XIII) representing further aspects of the present invention set out above, $R_1$ and/or $R_2$ may take any of the preferred features of substituents $R_1$ and $R_2$ incorporated in compounds according to the first aspect of the present invention. It will therefore be appreciated that the present methods represent preferred synthetic pathways to producing preferred embodiments of compounds according to the first aspect of the present invention.

The present methods preferably employ a Suzuki-type reaction pathway wherein an aryl-boronic acid is reacted with an aryl-halide to generate compounds according to the first aspect of the present invention. Any appropriate reaction conditions may be employed but it is preferred that the reaction is catalysed using an appropriate catalyst, such as a palladium catalyst, as is well known in general Suzuki reaction methodology. Thus the reaction is preferably effected in the presence of a palladium catalyst, such as $Pd(PPh_3)_4$. Any suitable reaction temperature may be employed, but it is preferably above room temperature, more preferably above around 40 to 50° C., still more preferably at a temperature of around 60 to 100° C., and most preferably at a temperature of around 80° C. The reaction may be effected over any desirable time period. Preferably the reaction is effected over a time period of more than around 6 hours, more preferably more than around 12 hours and preferably less than around 36 to 48 hours. A preferred reaction time period is around 12 to 48 hours, still more preferably around 24 hours.

The aryl-halide starting material may be produced according to the following exemplary reaction scheme or derivatives thereof as would be apparent to the skilled person:

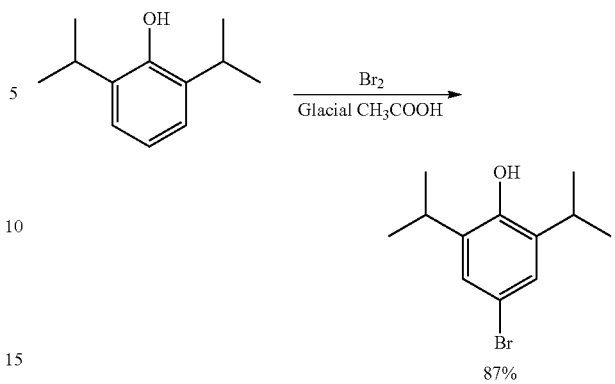

which may then be reacted with the appropriate aryl- or heteroaryl-boronic acid to generate the desired propofol analogue as exemplified below:

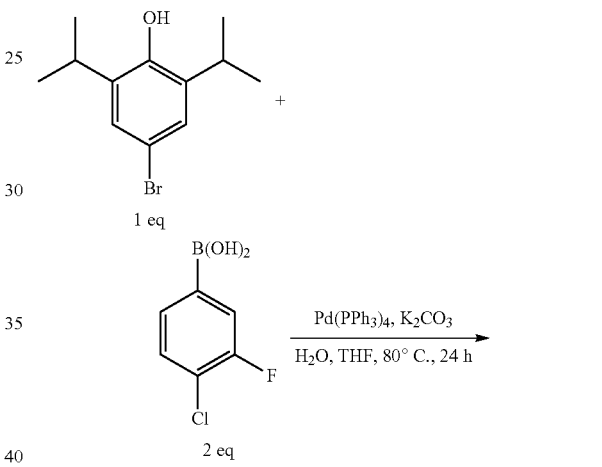

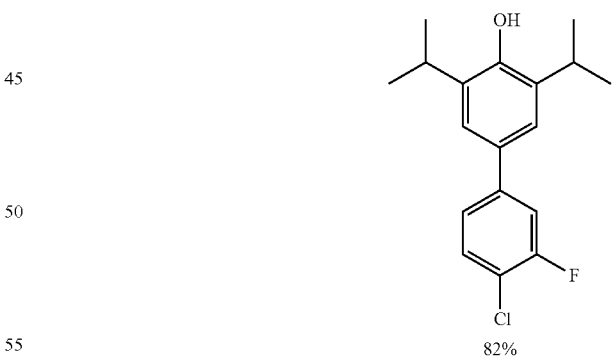

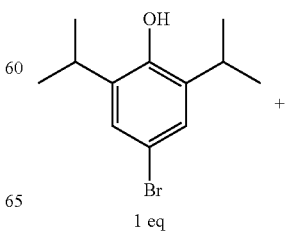

-continued

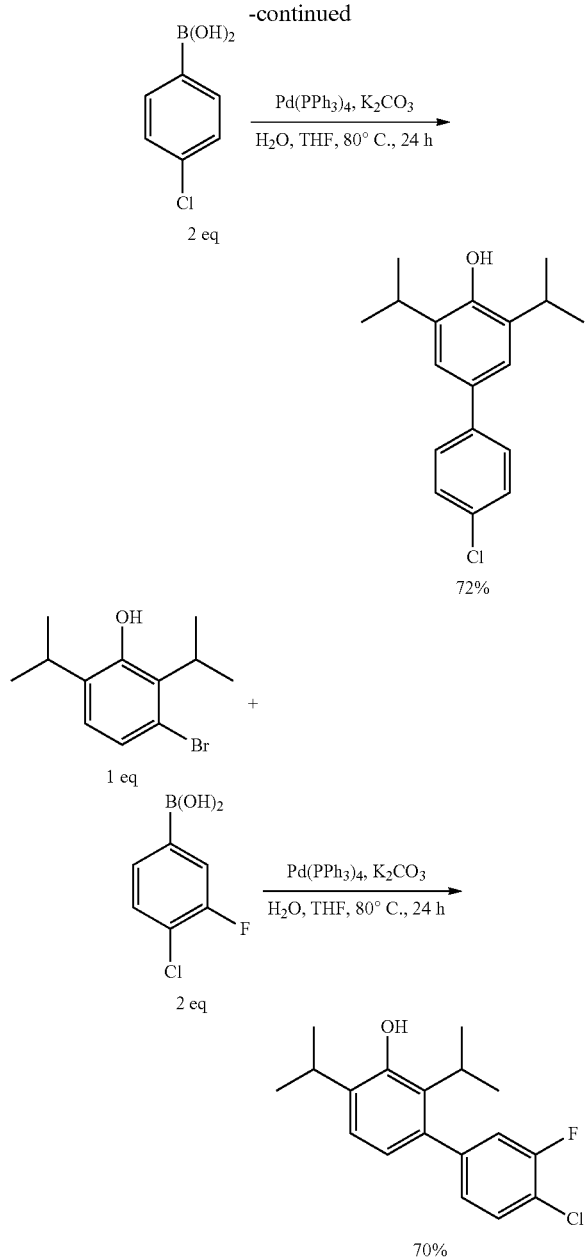

Compounds according to the invention, and pharmaceutical compositions and medicaments containing such compounds may be used as analgesics in a number of circumstances.

The compounds are particularly useful for targeting chronic pain states (e.g. neuropathic and/or post-inflammatory chronic pain) that, so far, have been notoriously difficult to treat. The compounds are particularly useful for treating chronic neuropathic pain which is hard to treat with conventional drugs such as NSAIDs, opiate deriatives etc The compounds are also useful for treating acute pain (e.g. following injury).

The compounds of the invention are also beneficial because they avoid all the familiar side effects of local anaesthetics and analgesics as well as NSAIDs and opioids if used as a monotherapy while, at the same time, allowing a vast variety of combined treatment strategies aiming at additive or supra-additive effects.

Examples of specific conditions in which pain may be modulated include chronic lower back pain, arthritis, cancer pain, trigeminal neuralgia, stroke and neuropathic pain.

The compounds may be used to treat existing pain but may also be used when prophylactic treatment is considered medically necessary, for instance, in advance of elective surgery.

The compounds may be used as an analgesic in the form of a monotherapy (i.e., use of the compound alone) or alternatively the compounds may be given in combination with other treatments that also reduce pain. Preferred combination therapy involves the use of the compounds with analgesics that modulate pain by a pain processing pathway that is different to pathway modulated by compounds of general formula. Such analgesics include morphine, paracetamol, and NSAIDS. The compounds may also be usefully combined with local anaesthetics (e.g. lignocaine) that only indirectly interact with glycine receptors.

The medicaments of the invention may comprise a compound of general formula I or IA and a pharmaceutically acceptable vehicle. It will be appreciated that the vehicle should be one which is well tolerated by the subject to whom it is given and enables delivery of the compounds to the affected area.

The medicaments of the invention may take a number of different forms depending, in particular on the manner in which the compound is to be used. Thus, for example, the medicament may comprise a compound in the form of a salt of the phenol derivative (e.g. a sodium salt). Such salts may be manufactured in a powder form and incorporated in a tablet, capsule, liquid, ointment, cream, gel, hydrogel, aerosol, spray, micelle, transdermal patch, liposome or any other suitable form that may be administered to a person or animal.

Alternatively the phenol derivative according to the invention may be dissolved in a suitable solvent to form a liquid medicament. The solvent may be aqueous (e.g. PBS or distilled water). Alternatively the solvent may be an alcohol such as ethanol or a mixture of such a solvent with an aqueous solvent.

It is preferred that the medicament is used for topical or local treatment. Such medicaments may be formulated as a liquid for application to an effected site. Alternatively the liquid may be formulated for administration by injection or as an aerosol.

The compound may also be incorporated within a slow or delayed release device. Such devices may, for example, be inserted on or under the skin and the compound may be released over weeks or even months. Such a device may be particularly useful for patients with long-term chronic pain (e.g. a patient with arthritis). The devices may be particularly advantageous when a compound is used which would normally require frequent administration.

It will be appreciated that the amount of a compound required is determined by biological activity and bioavailability which in turn depends on the mode of administration, the physicochemical properties of the compound employed and whether the compound is being used as a monotherapy or in a combined therapy. The frequency of administration will also be influenced by the abovementioned factors and particularly the half-life of the compound within the subject being treated.

Optimal dosages to be administered may be determined by those skilled in the art, and will vary with the particular compound in use, the strength of the preparation, the mode of administration, and the extent of the pain requiring relief. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of compositions and precise therapeutic regimes (such as daily doses of the compounds and the frequency of administration).

Generally, a dose should be given that is effective for delivering a compound at the target site such that the tissue concentration is around the $EC_{50}$ of the compound used. Daily doses may be given as a single administration (e.g. as a single daily injection). Alternatively, the compound used may require administration twice or more times during a day. As an example, preferred compounds for treating chronic lower back pain may be administered as two (or more depending upon the severity of the pain) daily doses of an injectable solution or an ointment. A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

This invention further provides a pharmaceutical composition comprising a therapeutically effective amount of the compound of the invention and a pharmaceutically acceptable vehicle. In one embodiment, the amount of a salt of a phenol derivative according to the present invention is an amount from about 10 µg/kg Body Weight to 10 mg/kg Body Weight in each dose unit for enteral (oral, rectal) administration. In another embodiment, the amount is from about 1 µg/kg Body Weight to 1 mg/kg Body Weight in each dose unit for parenteral (intravenous/intrathecal or epidural) administration.

In a further embodiment, the vehicle is a liquid and the composition is a solution. Useful liquid solutions for parenteral administration may comprise between 0.001 and 1% by weight of the phenols of formula I or IA. In another embodiment, the vehicle is a solid and the composition is a tablet. In a further embodiment, the vehicle is a gel and the composition is for topical application.

In the subject invention a "therapeutically effective amount" is any amount of a compound, medicament or composition which, when administered to a subject suffering from a painful condition against which the compounds are effective, causes reduction, remission, or regression of the pain.

A "subject" is a vertebrate, mammal, domestic animal or human being.

In the practice of this invention the "pharmaceutically acceptable vehicle" is any physiological vehicle known to those of ordinary skill in the art useful in formulating pharmaceutical compositions. In one embodiment, the pharmaceutical vehicle may be a liquid and the pharmaceutical composition would be in the form of a solution. In another embodiment, the pharmaceutically acceptable vehicle is a solid and the composition is in the form of a powder or tablet. In a further embodiment, the pharmaceutical vehicle is a gel and the composition is in the form of a suppository or cream. In a further embodiment the compound or composition may be formulated as a part of a pharmaceutically acceptable transdermal patch.

A solid vehicle can include one or more substances which may also act as lubricants, solubilizers, suspending agents, fillers, glidants, compression aids, binders or tablet-disintegrating agents; it can also be an encapsulating material. In powders, the vehicle is a finely divided solid which is in admixture with the finely divided active ingredient. In tablets, the active ingredient is mixed with a vehicle having the necessary compression properties in suitable proportions and compacted in the shape and size desired. The powders and tablets preferably contain up to 99% of the active ingredient. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Liquid vehicles are used in preparing solutions, suspensions, emulsions and the like. The phenol derivative can be dissolved or suspended in a pharmaceutically acceptable liquid vehicle such as water, ethanol, an organic solvent or mixtures thereof or pharmaceutically acceptable oils or fats.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium.

Figure 2:
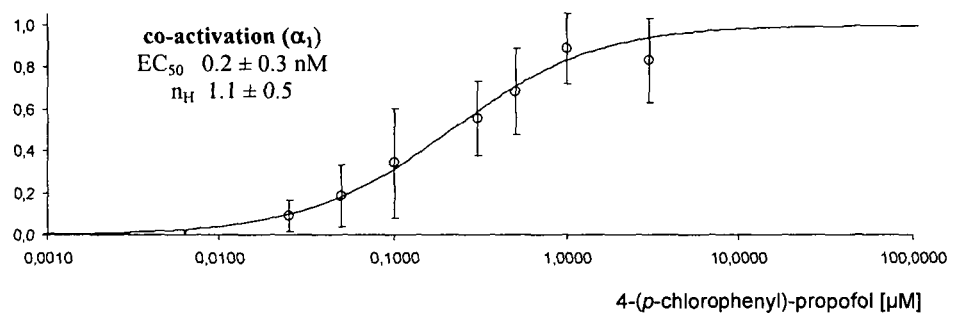
Figure 3:
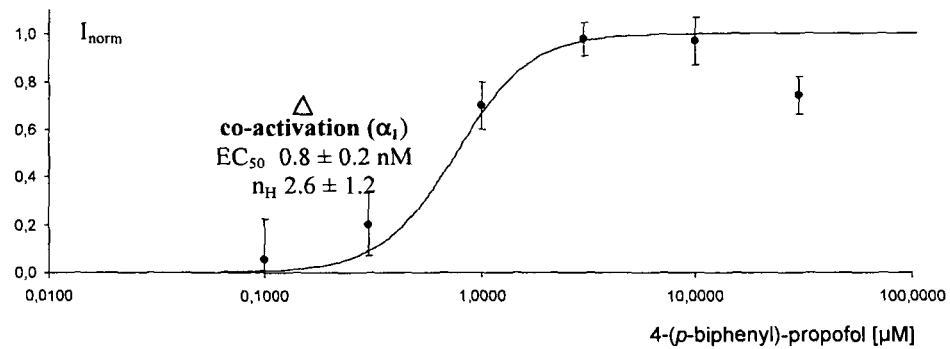
Figure 4:
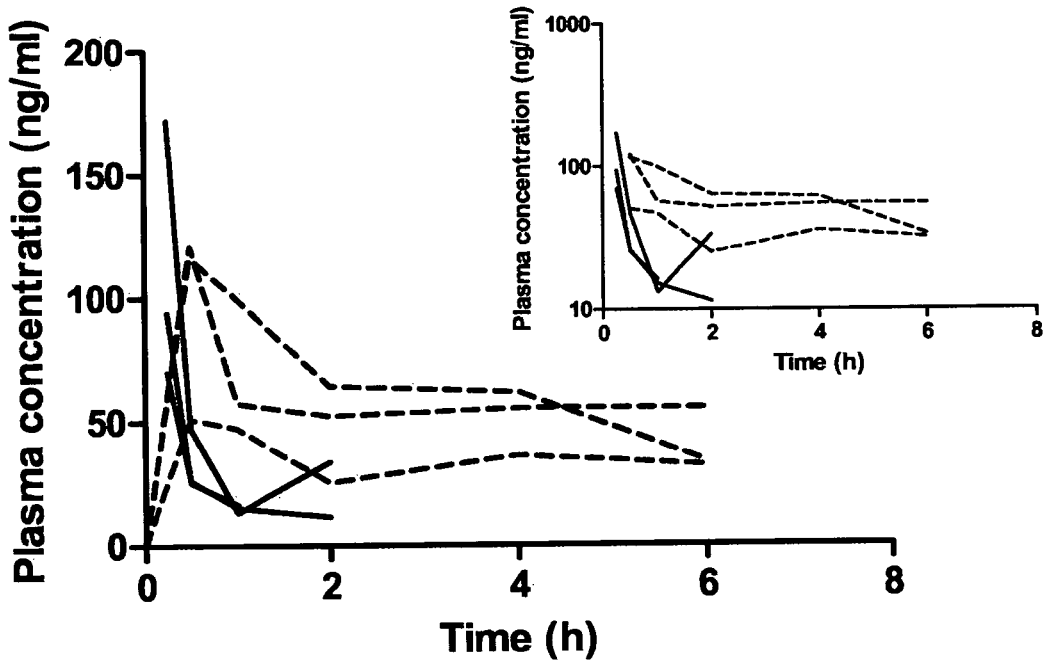
Figure 5:
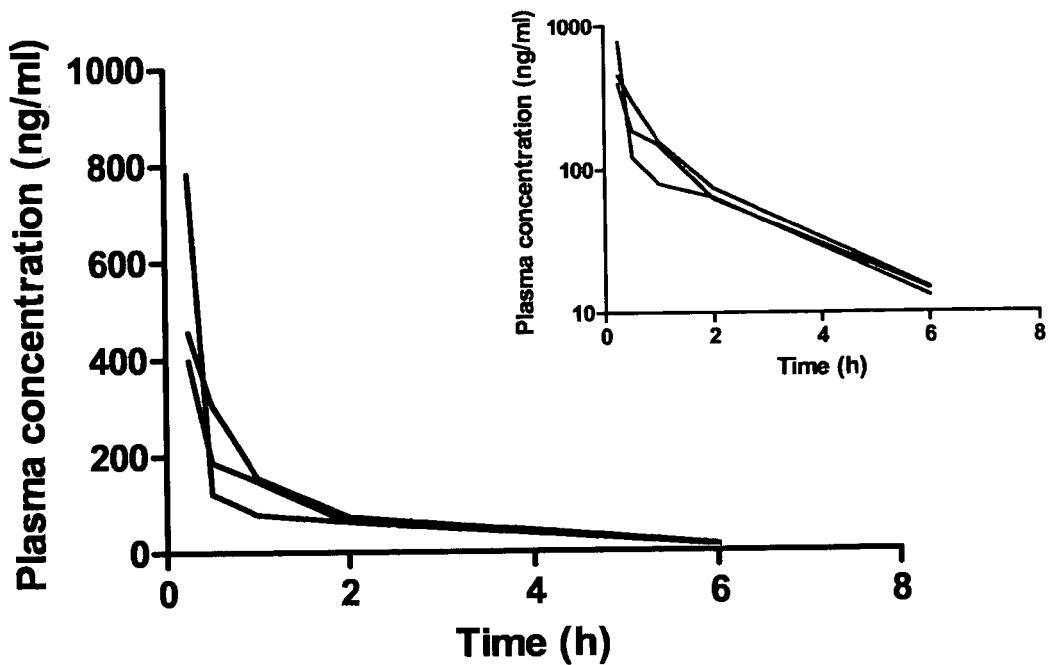

The present invention will now be illustrated further by the following Examples and with reference to the following drawings, in which:

FIG. 1: Normalized Cl⁻ current activated in the absence of glycine via $\alpha_1$ homomeric glycine receptors (mean±SD; n=3 each), plotted against the concentration of 4-(p-tert-butylphenyl)-propofol on a logarithmic scale. Currents were normalized either to maximum value achieved by high concentrations of the compound. Solid lines are Hill fits to the data with the indicated parameters;

FIG. 2: Normalized Cl⁻ current activated in the absence of glycine via $\alpha_1$ homomeric glycine receptors (mean±SD; n=3 each), plotted against the concentration of 4-(p-chlorophenyl)-propofol on a logarithmic scale. Currents were normalized either to maximum value achieved by high concentrations of the compound. Solid lines are Hill fits to the data with the indicated parameters;

FIG. 3: Normalized Cl⁻ current activated in the absence of glycine via $\alpha_1$ homomeric glycine receptors (mean±SD; n=3 each), plotted against the concentration of 4-(p-biphenyl)-propofol on a logarithmic scale. Currents were normalized either to maximum value achieved by high concentrations of the compound. Solid lines are Hill fits to the data with the indicated parameters;

FIG. 4: Plasma concentrations of individual animals for CK-I-I after p.o. (broken lines) and i.v. (solid lines) administration of 8 mg/kg and 1 mg/kg, respectively. Inset depicts the same data on a semilogarithmic scale;

FIG. 5: Plasma concentrations of individual animals for CK-2-3 after i.v. administration of 20 mg/kg and 2 mg/kg, respectively. Inset depicts the same data on a semilogarithmic scale. Compound was not detected in plasma after p.o. administration; and FIG. 6: Plasma concentrations of individual animals for CK-2-9 after p.o. (broken lines) and i.v. (solid lines) administration of 20 mg/kg and 2 mg/kg, respectively. Inset depicts the same data on a semilogarithmic scale.

Figure 7:
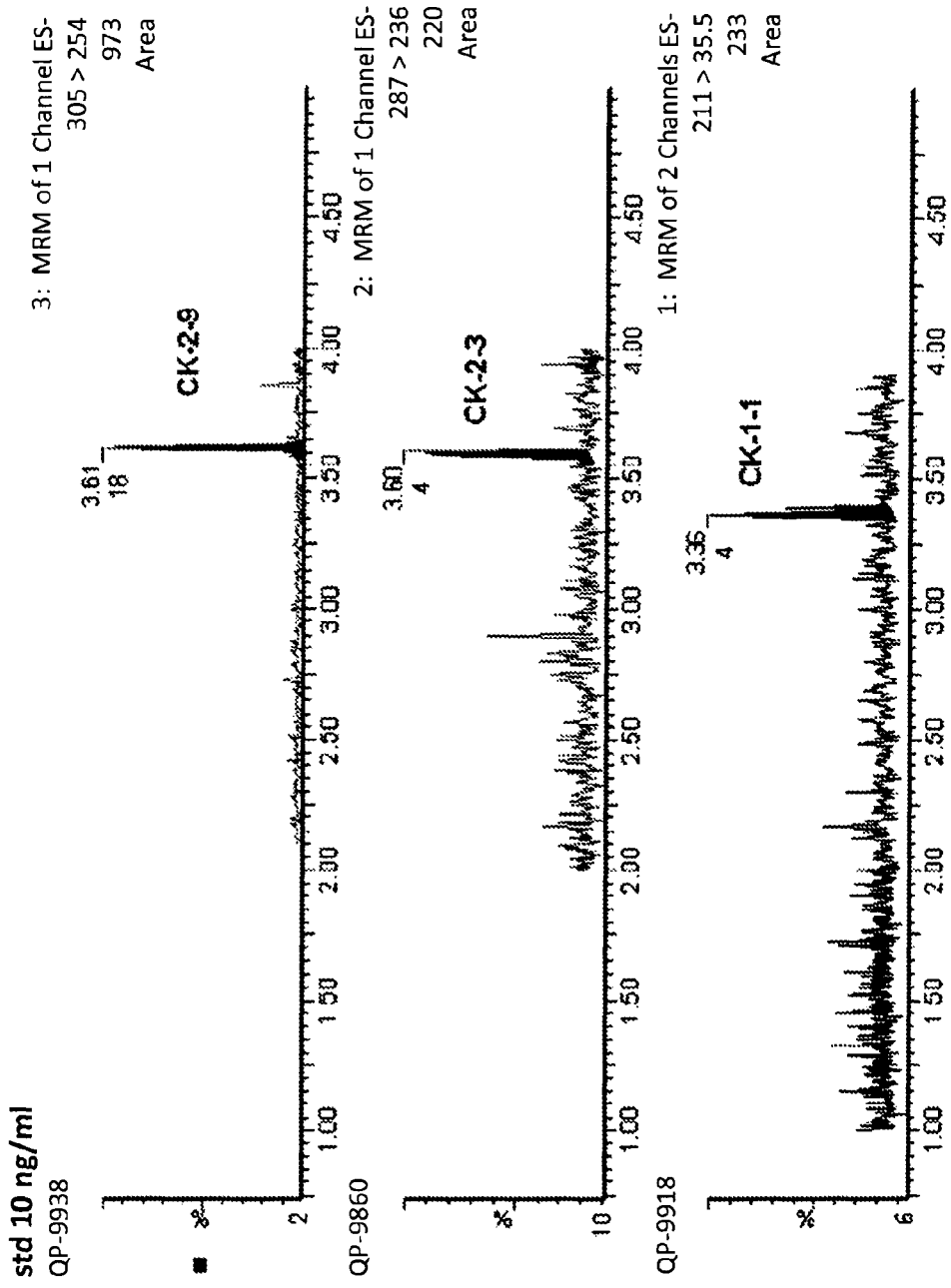

FIG. 7: The performance ("on-the-fly validation") of the analytical method is shown in FIG. 7 with examples of the LC/MS/MS chromatograms.

EXAMPLES

A large number of aryl-substituted propofol analogues in accordance with the present invention have been synthesised as described below starting from various halo-substituted propofol compounds. The aryl-substituted analogues produced were then tested for their solubility in ethanol, before a representative selection were tested to determine their $EC_{50}$ values and Hill coefficients.

Compound Synthesis

Synthesis of 4-Substituted Propofol Analogues

4-Bromopropofol:

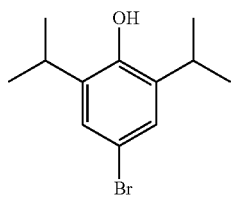

Propofol (1 g, 5.6 mmol) was dissolved in glacial acetic acid (25 ml.) Bromine (aq) was added dropwise with stirring until discolouration of the solution ceased. The mixture was left stirring at room temperature for one hour. The reaction mixture was then slowly poured onto water (50 ml.) The resultant red oil was extracted with ethyl acetate and washed with water and brine. The crude product was dried over magnesium sulphate and solvent removed to give a brown oil which was purified by flash chromatography using 2% DCM in hexane as eluent. 1.35 g of a pale yellow oil was recovered as pure 4-bromo-propofol (93%.) $^1$H NMR 400 MHz d 7.1 (s, 1H), 4.75 (s, 1H), 3.15 (m, 2H), 1.3 (d, 12H). $^{13}$C NMR d 149.4, 136.48, 126.89, 113.74, 27.69, 22.95. HRMS (EI) $C_{12}H_{17}OBr$ [M+H]$^+$ requires 258.1679, found 258.1703. Anal. $C_{12}H_{17}OBr$ requires C: 56.04% H: 6.66% found C: 55.99% H: 6.63%.

4-Nitro-propofol:

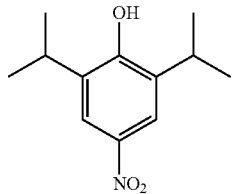

Propofol (1.78 g, 10 mmol.) was dissolved in a mixture of AcOH: DCM 15:10 mL. Nitric acid (1 mL dissolved in 10 mL DCM) was added dropwise at 0° C. A colour change of yellow to orange to red was observed on addition. Water (20 mL) was added and the reaction mixture was extracted with DCM (3×20 mL). The resultant red solution was dried over sodium sulphate and solvent removed to give a dark red crude solid. The crude product was purified via recrystallisation from diethyl ether and hexane to give pale yellow crystals in two crops. 1.803 g (84%). $^1$H NMR δ 7.71 (s, 2H), 4.77 (s, 1H), 3.1 (m, 2H), 1.3 (d, 12H). $^{13}$C NMR δ 155.21, 140.44, 138.41, 120.20, 27.68, 23.01. HRMS (EI) $C_{12}H_{20}N_2O_3$ [M+NH4]$^+$ requires 240.2735 found 240.2731. Anal. $C_{12}H_{16}NO_3$ requires C: 64.55% H: 7.67% N: 6.27%. Found C: 64.53% H: 7.66% N: 6.25%.

4-Amino-propofol:

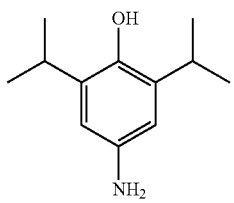

4-Nitropropofol (0.368 g, 1.6 mmol) was dissolved in EtOH (2.8 mL) and concentrated HCl (7.5 mL.) An excess of tin granules (1.4 g) was added and the reaction mixture was heated to reflux. A colour change from pale yellow to colourless was observed. After one hr, the reaction mixture was filtered through a cellite pad. Solvent was removed under reduced pressure and the resultant residue was redissolved in water (50 ml). Aqueous sodium hydroxide was added dropwise until the solution was basic by universal indicator paper, (pH 12-15). The solution was then extracted with DCM (3×25 mL). The organic extracts were combined, washed with brine, dried over sodium sulphate and the solvent removed to give 320 mg of analytically pure purple oil 98%. $^1$H NMR δ 6.45 (s, 2H), 4.75 (s, 1H) 3.4 (br s, 2H) 3.1 (m, 2H) 1.3 (d, 12H). $^{13}$C NMR δ 140.45, 138.72, 136.48, 112.02, 27.70, 23.01. HRMS (CI) $C_{12}H_{22}N_2O$ [M+NH$_4$]$^+$ requires 210.3093 found 210.3097. Anal $C_{12}H_{18}NO$ requires C: 74.56% H: 9.91% N: 7.24% found C: 74.36% H: 9.95% N: 7.23%.

4-Aminopropofol-hydrochloride:

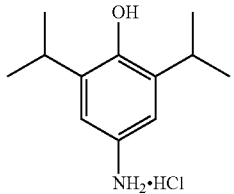

4-Amino propofol (310 mg, 1.6 mmol) was dissolved in $Et_2O$ (100 mL). Concentrated HCl (5 mL) dissolved in 1,4-dioxane (25 mL) was added dropwise with stirring. After 1 Hr the mixture is allowed to settle into two layers, the bottom layer is recovered and solvent removed under reduce pressure to a pink crystalline solid (250 mg, 67%) and is used without further analysis.

4-Trifluoroacetamide-propofol:

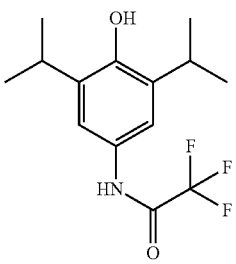 [SMILES: CC(C)c1cc(NC(=O)C(F)(F)F)cc(C(C)C)c1O]

4-Aminopropofol (200 mg, 1.04 mmol) was dissolved in EtOAc (40 mL). Pyridine (0.25 mL, 3 mmol) was added followed by trifluoroacetic anhydride (0.2 mL, 1 mmol). The reaction mixture was heated to 60° C. for 30 mins. Upon cooling, solvent was removed under reduced pressure, the residue was redissolved in DCM (50 mL), washed successively with water and brine and dried over sodium sulphate. After removal of solvent, 4-trifluoroacetamidopropofol was recovered as a pale pink crystalline solid (205 mg, 75%). $^1$H NMR δ 7.16 (s, 2H), 6.3 (br s, 1H), 5.0 (1H, s), 3.2 (m, 2H), 1.3 (d, J=6.9 Hz, 12H). $^{13}$C NMR δ 155.18, 144.28, 138.05, 130.51, 117.03, 115.85, 27.78, 23.12. HRMS (EI): $C_{14}H_{18}F_3NO_2$ [M+H]$^+$ requires 306.2751, found 306.2747. Anal. $C_{14}H_{18}F_3NO_2$ requires C: 58.12, H: 6.27, N, 4.84, found C: 58.11, H: 6.25, N: 4.83.

4-Chloropropofol:

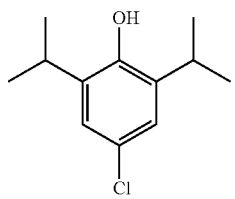

Propofol (710 mg, 4.0 mmol) was dissolved in DCM. Sulfuryl chloride (0.675 g, 5 mmol) was added dropwise, and then the reaction mixture was refluxed for 4 hrs. Solvent was removed under reduce pressure to give crude product as a brown oil which was purified by distillation to give 4-chloropropofol as a pale orange oil (750 mg, 89%) b.p. 94-97° C. at 1 mm Hg. $^1$H NMR δ 7.0 (s, 2H), 5.0 (s, 1H), 3.1 (m, 2H), 1.2 (d, J=6.9 Hz, 2H). $^{13}$C NMR δ 148.92, 139.12, 126.12, 124.01, 27.37, 22.68. HRMS (EI) $C_{12}H_{17}OCl$ [M+H]$^+$ requires 166.9545, found 166.9572. Anal. $C_{12}H_{17}OCl$ requires C: 67.76, H: 8.06, found C: 67.70, H: 8.04.

Synthesis of Aryl-Substituted Propofol Anolgues 4-(para-Chlorophenyl)-propofol:

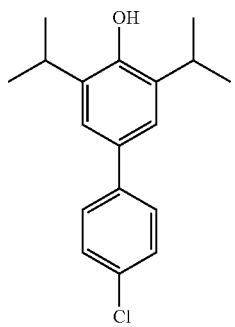

A suspension of 4-bromo-propofol (200 mg, 0.77 mmol), para-chlorophenylboronic acid (156 mg, 1 mmol, 1.3 eq), tetrakis (triphenylphosphine) palladium (0) (26 mg, 3 mol %), sodium carbonate (3.5 mL of a 2 N aqueous solution) and dimethoxyethane (10 mL) was stirred for 24 hrs at 95° C. The suspension was cooled, filtered through cellite, dissolved in EtOAc, successively washed in water and brine, dried over sodium sulphate and solvent removed in vacuo. Purification of the resultant residue by column chromatography eluted in 10% EtOAc in Hexane gave pure product as a white solid (72%%). $^1$H NMR δ 7.5-7.2 (m, 6H), 4.8 (s, 1H), 3.2 (m, 2H), 1.3 (d, J=6.85 Hz, 12H). $^{13}$C NMR δ 147.59, 138.23, 134.54, 132.89, 129.11, 128.50. 122.71, 27.71, 23.144. HRMS: (EI)$^-$ $C_{18}H_{20}OCl$ [M+H]$^-$ requires 287.1203, found 287.1206. Anal. $C_{18}H_{20}OCl$ requires C: 74.86, H: 7.33, found C: 74.88, H: 7.32

4-(para-carbamoylphenyl)-propofol:

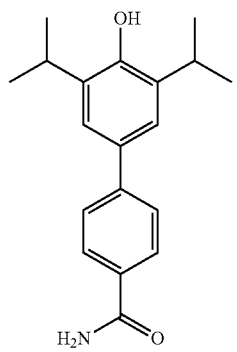 [SMILES: CC(C)c1cc(-c2ccc(C(N)=O)cc2)cc(C(C)C)c1O]

4-bromopropofol (200 mg, 0.77 mmol), p-carbamoyl phenyl boronic acid and tetrakis (triphenylphosphine) palladium (0) were reacted according to general procedure A to give product as a pale yellow solid (212 mg, 93%). $^1$H NMR δ 8.00-7.7 (m, 4H), 7.2 (s, 2H), 6.3 (s, 2H) 5.1 (s, 1H) 3.2 (m, 2H), 1.2 (d, J=6.85, 12H). $^{13}$C NMR δ 168.13, 147.55, 139.90, 138.18, 133.07, 128.05, 127.94, 126.53, 26.71, 23.68. HRMS (EI)$^-$ $C_{19}H_{23}NO_2$[M+H]$^-$ requires 298.4567, found 298.4570. Anal. $C_{19}H_{23}NO_2$ requires C: 76.73, H: 7.80; N: 4.71, found C 76.70, H: 7.76, N, 4.68.

4-(p-tert-butylphenyl)-propofol:

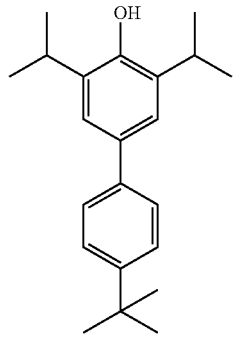 [SMILES: CC(C)c1cc(-c2ccc(C(C)(C)C)cc2)cc(C(C)C)c1O]

4-bromopropofol (300 mg, 1.12 mmol), p-tert-butyl phenyl boronic acid and tetrakis (triphenylphosphine) palladium (0) were reacted according to general procedure A to give product as yellow oil (300 mg, 83%). $^1$H NMR δ 74-7.2 (m, 6H), 4.9 (s, 1H), 3.15 (m, 2H), 1.4 (s, 9H), 1.2 ppm (d, J=6.85, 12H). $^{13}$C NMR δ 149.00, 147.63, 138.21, 133.38, 128.49, 127.58, 126.45, 125.30, 40.67, 31.39, 26.70, 23.65. HRMS (EI) $C_{22}H_{30}O$ [M+H]$^+$ requires 310.4690, found 310.4692. Anal. $C_{22}H_{30}O$ requires C: 85.11, H: 9.74, found C: 85.10, 9.72.

4-(para-Fluorophenyl)-propofol:

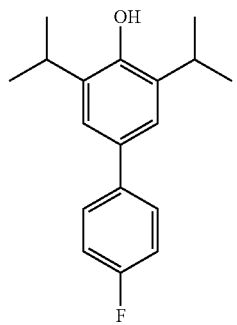 [SMILES: CC(C)c1cc(-c2ccc(F)cc2)cc(C(C)C)c1O]

4-bromopropofol (300 mg, 1.12 mmol), p-fluoro phenyl boronic acid and tetrakis (triphenylphosphine) palladium (0) were reacted according to general procedure A to give product as pale yellow oil (210 mg, 69%). $^1$H NMR δ 7.6 (m, 2H), 7.2 (m, 4H), 4.85 (s, 1H), 3.2 (m, 2H), 1.25 ppm (d, J=6.85, 12H). $^{13}$C NMR δ 150.39, 141.13, 134.55, 132.79, 128.52, 122.85, 121.50, 100.00, 27.77, 23.14. HRMS: (EI) $C_{18}H_{21}FO$ [M+H]$^+$ requires 273.3598, found 273.3593. Anal. $C_{18}H_{21}FO$ requires C, 79.38, H: 7.77, found C: 79.30, H: 7.76.

4-(p-trifluoromethoxyphenyl)-propofol:

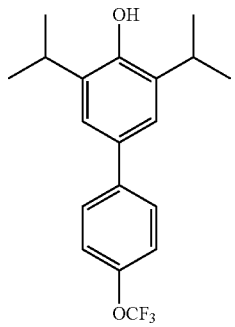 [SMILES: CC(C)c1cc(-c2ccc(OC(F)(F)F)cc2)cc(C(C)C)c1O]

4-bromopropofol (200 mg, 0.77 mmol), p-trifluoromethoxy phenyl boronic acid and tetrakis (triphenylphosphine) palladium (0) were reacted according to general procedure A to give product as a pale yellow solid (205 mg, 79%). $^1$H NMR δ 7.6-7.5 (m, 2H), 7.3-7.0 (m, 4H), 4.8 (s, 1H), 3.2 (m, 2H), 1.3 ppm (d, J=6.85, 12H). $^{13}$C NMR δ 159.62, 150.05, 134.46, 128.79, 128.71, 122.74, 115.88, 115.67, 99.99, 27.77, 23.16. HRMS (EI)$^-$ $C_{19}H_{21}F_3O_2$ [M+H]$^-$ requires 339.3568, found 339.3564. Anal. $C_{19}H_{21}F_3O_2$ requires C: 67.44, H: 6.26, found C: 67.40; H: 6.23.

4-(p-biphenyl)-propofol:

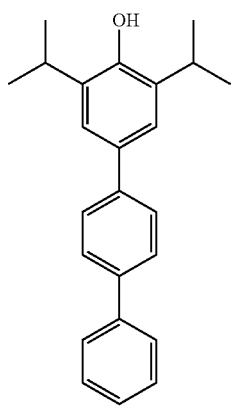 [SMILES: CC(C)c1cc(-c2ccc(-c3ccccc3)cc2)cc(C(C)C)c1O]

4-bromopropofol (200 mg, 0.77 mmol), p-biphenyl boronic acid and tetrakis (triphenylphosphine) palladium (0) were reacted according to general procedure A to give product as an off white solid (100 mg, 39%). $^1$H NMR δ 7.6 (s, 4H), 7.5 (m, 2H), 7.2-7.3 (m, 3H), 7.0 (s, 2H), 4.9 (s, 1H), 3.1 (m, 2H), 1.2 ppm (d, J=6.85, 12H). $^{13}$C NMR δ147.53, 138.18, 136.5, 135.40, 135.31, 129.41, 128.43, 128.0, 127.3, 126.3, 26.73, 23.73. HRMS: (EI) $C_{24}H_{26}O$ [M+H]$^+$ requires 331.4673, found 331.4663. Anal. $C_{24}H_{26}O$ requires C: 87.23; H: 7.93; O: 4.84, found C: 87.18, H: 7.76, O: 4.79 p-(4-Fluoro,3-Chlorophenyl)-propofol:

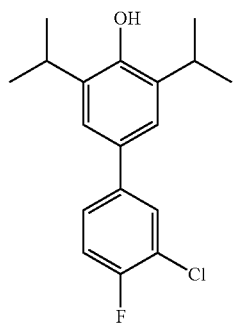 [SMILES: CC(C)c1cc(-c2ccc(F)c(Cl)c2)cc(C(C)C)c1O]

4-Bromopropofol (200 mg, 0.77 mmol), 4-fluoro,3-chlorophenyl boronic acid and tetrakis (triphenylphosphine) palladium (0) were reacted according to general procedure A to give product as a pale yellow solid (82%). $^1$H NMR δ7.35-7.25 (m, 3H), 7.0-6.9 (m, 3H), 4.85 (s, 1H), 3.2 (m, 2H), 1.25 ppm (d, J=6.85, 12H). $^{13}$C NMR δ161.81, 147.58, 138.31, 133.47, 129.56, 128.59, 127.39, 126.50, 121.28, 117.30, 25.95, 22.89. HRMS: (EI) $C_{18}H_{20}ClFO$ [M+H]$^+$ requires 307.8139, found 307.8090. Anal. $C_{18}H_{20}ClFO$ requires C: 70.47, H: 6.57, found C: 70.50, H, 6.63.

Para-(2,3-dichlorophenyl)-propofol:

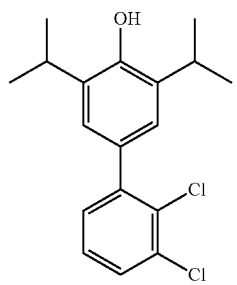 [SMILES: CC(C)c1cc(-c2cccc(Cl)c2Cl)cc(C(C)C)c1O]

4-Bromopropofol (200 mg, 0.77 mmol), 2,3-dichlorophenyl boronic acid and tetrakis (triphenylphosphine) palladium (0) were reacted according to general procedure A to give product as a white solid (170 mg, 68%). $^1$H NMR δ7.25-7.15 (m, 3H), 7.0 (s, 2H) 4.85 (s, 1H), 3.20 (m, 2H), 1.3 ppm (d, J=6.85, 12H). $^{13}$C NMR δ147.58, 138.78, 138.17, 134.01, 131.63, 129.25, 128.45, 127.43, 126.49, 26.68, 23.72. HRMS: (EI) $C_{18}H_{20}Cl_2$ [M+H]$^+$ requires 324.2679, found 324.2674. Anal. $C_{18}H_{20}Cl_2O$ requires C: 66.88, H, 6.24, found C, 66.93, H, 6.30.

Para-(2,3-difluorophenyl)-propofol:

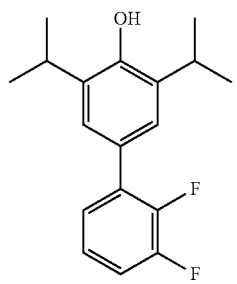 [SMILES: CC(C)c1cc(-c2cccc(F)c2F)cc(C(C)C)c1O]

4-Bromopropofol (300 mg, 1.12 mmol), 2,3-difluorophenyl boronic acid and tetrakis (triphenylphosphine) palladium (0) were reacted according to general procedure A to give product as a white solid (290 mg, 89%). $^1$H NMR δ7.15-6.9 (m, 5H), 4.85 (s, 1H), 3.15 (m, 2H), 1.3 ppm (d, J=6.85, 12H). $^{13}$C NMR δ151.01, 147.78, 145.58, 138.19, 133.07, 128.53, 126.48, 125.10, 116.03, 26.60, 23.74. HRMS: (EI) $C_{18}H_{20}F_2O$ [M+H]$^+$ requires 291.3589, found 291.3591. Anal. $C_{18}H_{20}F_2O$ requires C, 74.46, H, 6.94, found C, 74.51, H, 6.99.

Para-(2-Fluoro, 3-chlorophenyl)-propofol:

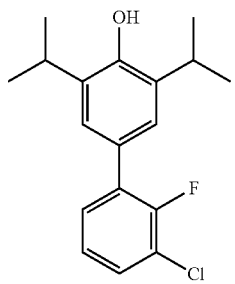

4-Bromopropofol (520 mg, 1.94 mmol), 2-fluoro,3-chlorophenyl boronic acid and tetrakis (triphenylphosphine) palladium (0) were reacted according to general procedure A to give product as yellow oil (520 mg, 95%). $^1$H NMR δ7.3-7.2 (m, 2H), 7.1-7.0 (m, 3H) 4.8 (s, 1H), 3.1 (m, 2H), 1.25 ppm (d, J=6.85, 12H). $^{13}$C NMR δ161.42, 147.59, 138.24, 132.66, 129.43, 128.46, 127.58, 126.54, 126.28, 121.30, 26.74, 23.68. HRMS: (EI) $C_{18}H_{20}ClFO$ [M+H]$^+$ requires 307.8139, found 307.8126. Anal. $C_{18}H_{20}ClFO$ requires C, 70.47; H: 6.57, found C: 70.43, H: 6.54.

Para-(3,5-difluorophenyl)-propofol:

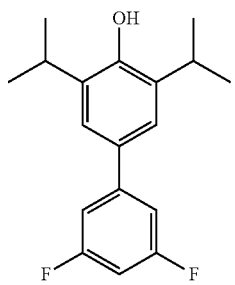

4-Bromopropofol (520 mg, 1.94 mmol), 3,5-difluorophenyl boronic acid and tetrakis (triphenylphosphine) palladium (0) were reacted according to general procedure A to give product as deep red oil (500 mg, 89%). $^1$H NMR δ7.3-7.2 (m, 2H), 7.0-6.9 (m, 4H) 6.6 (m, 1H), 4.9 (s, 1H), 3.15 (m, 2H), 1.3 ppm (d, J=6.85, 12H). $^{13}$C NMR δ165.00, 147.58, 139.80, 138.16, 128.54, 126.48, 120.01, 103.63, 26.59, 23.64. HRMS: (EI) $C_{18}H_{20}F_2O$ [M+H]$^+$ requires 291.3589, found 291.3580. Anal. $C_{18}H_{20}F_2O$ requires C: 74.46, H: 6.94, found C: 74.40; H: 6.88.

Para-(3,5-dichlorophenyl)-propofol:

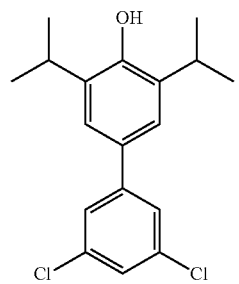 [SMILES: CC(C)c1cc(-c2cc(Cl)cc(Cl)c2)cc(C(C)C)c1O]

4-Bromopropofol (200 mg, 0.77 mmol), 3,5-dichlorophenyl boronic acid and tetrakis (triphenylphosphine) palladium (0) were reacted according to general procedure A to give product as a yellow semisolid (200 mg, 80%). $^1$H NMR δ7.4 (s, 2H), 7.2 (s, 1H) 7.0 (s, 1H), 4.8 (s, 1H), 3.1 (m, 2H), 1.2 ppm (d, J=6.85, 12H). $^{13}$C NMR δ147.62, 139.34, 138.15, 136.21, 129.30, 126.48, 125.87, 26.63, 23.74. HRMS: (EI) $C_{18}H_{20}Cl_2O$ [M+H]$^+$ requires 324.2679, found 324.2649. Anal. $C_{18}H_{20}Cl_2O$ requires C: 66.88, H: 6.24, found C: 66.80, H: 6.28.

Para-(3,5-di-trifluoromethylphenyl)-propofol:

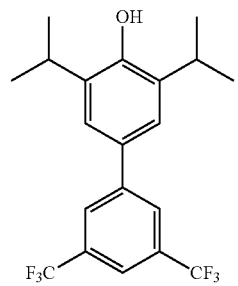 [SMILES: CC(C)c1cc(-c2cc(C(F)(F)F)cc(C(F)(F)F)c2)cc(C(C)C)c1O]

4-Bromopropofol (300 mg, 1.12 mmol), 3,5-di-trifluoromethylphenyl boronic acid and tetrakis (triphenylphosphine) palladium (0) were reacted according to general procedure A to give product as a yellow semisolid (350 mg, 80%). $^1$H NMR δ7.7-7.6 (m, 3H) 7.0 (s, 1H), 4.8 (s, 1H), 3.15 (m, 2H), 1.25 ppm (d, J=6.85, 12H). $^{13}$C NMR δ148.00, 138.75, 137.21, 131.92, 130.33, 128.83, 126.72, 125.03, 122.09, 27.10, 23.85. HRMS: (EI) $C_{20}H_{20}F_6O$ [M+H]$^+$ requires 391.3729, found 391.3721. Anal. $C_{20}H_{20}F_6O$ requires C: 61.54, H: 5.16, found C: 61.60, H: 5.19.

Para-(3,4-dichlorophenyl)-propofol:

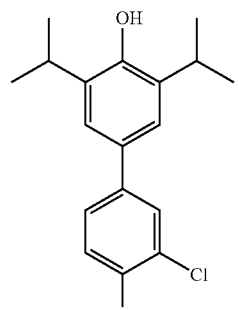

4-Bromopropofol (200 mg, 0.77 mmol), 3,4-dichlorophenyl boronic acid and tetrakis (triphenylphosphine) palladium (0) were reacted according to general procedure A to give product as a yellow semisolid (120 mg, 48%). $^1$H NMR δ7.4-7.3 (m, 3H) 7.15 (m, 1H), 4.9 (s, 1H), 3.25 (m, 2H), 1.3 ppm (d, J=6.85, 12H). $^{13}$C NMR δ148.01, 139.05, 136.31, 133.95, 130.78, 129.15, 128.56, 127.38, 126.41, 26.79, 23.69. $C_{18}H_{20}Cl_2O$ [M+H]$^+$ requires 324.2679, found 324.2656. Anal. $C_{18}H_{20}Cl_2O$ requires C: 66.88, H: 6.24, found C: 66.79, H: 6.23.

Para-(3-Fluoro,4-chlorophenyl)-propofol:

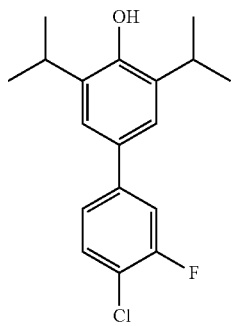

4-Bromopropofol (520 mg, 1.94 mmol), 3-fluoro,4-chlorophenyl boronic acid and tetrakis (triphenylphosphine) palladium (0) were reacted according to general procedure A to give product as a yellow solid (380 mg, 63%). $^1$H NMR δ7.3-7.1 (m, 5H), 5.0 (s, 1H), 3.2 (m, 2H), 1.3 ppm (d, J=6.85, 12H). $^{13}$C NMR δ163.28, 148.00, 138.24, 136.19, 131.02, 128.55, 125.99, 124.47, 119.73, 117.66, 26.80, 23.67. $C_{18}H_{20}ClFO$ [M+H]$^+$ requires 307.8079, found 307.8099. Anal. $C_{18}H_{20}ClFO$ requires C: 70.47, H: 6.57, found C: 70.43, H: 6.51.

Para-(3-fluorophenyl)-propofol:

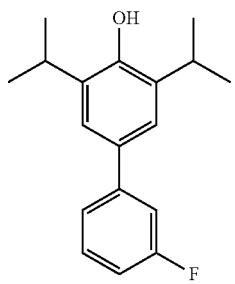

4-Bromopropofol (200 mg, 0.77 mmol), 3-fluorophenyl boronic acid and tetrakis (triphenylphosphine) palladium (0) were reacted according to general procedure A to give product as a pale pink solid (160 mg, 76%). $^1$H NMR δ7.25-6.9 (m, 6H), 5.1 (s, 1H), 3.25 (m, 2H), 1.2 ppm (d, J=6.85, 12H). $^{13}$C NMR δ163.44, 147.66, 138.17, 131.05, 128.47, 126.73, 123.44, 116.23, 114.01, 27.15, 22.99. $C_{18}H_{21}FO$ [M+H]$^+$ requires 273.3688, found 273.3680. Anal. $C_{18}H_{21}FO$ requires C: 79.38, H: 7.77, found C: 79.43, H, 7.81.

Para-(3-chlorophenyl)-propofol:

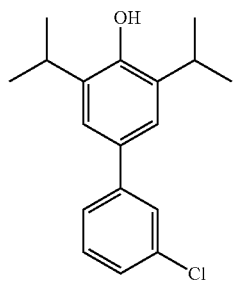 [SMILES: CC(C)c1cc(-c2cccc(Cl)c2)cc(C(C)C)c1O]

4-Bromopropofol (520 mg, 1.94 mmol), 3-chlorophenyl boronic acid and tetrakis (triphenylphosphine) palladium (0) were reacted according to general procedure A to give product as a pale yellow (350 mg, 62%). $^1$H NMR δ7.5 (s, 1H), 7.35-7.25 (m, 3H), 7.15 (s, 2H) 4.8 (s, 1H), 3.2 (m, 2H), 1.3 ppm (d, J=6.85, 12H). $^{13}$C NMR δ148.11, 138.34, 137.82, 134.91, 131.03. 129.03, 127.73, 125.99, 125.41, 27.09, 23.01. $C_{18}H_{21}ClO$ [M+H]$^+$ requires 289.8238, found 289.8245. Anal. $C_{18}H_{21}ClO$ requires C: 74.86, H: 7.33, found C: 74.72, H: 7.30.

Para-(3-trifluoromethoxyphenyl)-propofol:

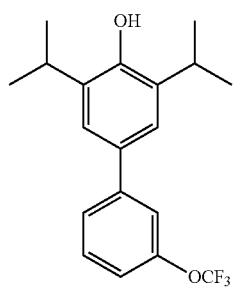 [SMILES: CC(C)c1cc(-c2cccc(OC(F)(F)F)c2)cc(C(C)C)c1O]

4-Bromopropofol (300 mg, 1.12 mmol), 3-chlorophenyl boronic acid and tetrakis (triphenylphosphine) palladium (0) were reacted according to general procedure A to give product as a pale yellow oil (230 mg, 56%). $^1$H NMR δ7.2 (m, 1H), 7.0 (m, 4H), 6.7 (m, 1H) 4.85 (s, 1H), 3.25 (m, 2H), 1.2 ppm (d, J=6.85, 12H). $^{13}$C NMR δ162.33, 148.41, 139.09, 137.71, 130.52, 129.12, 127.11, 121.79, 113.33, 26.68, 23.74. $C_{19}H_{21}F_3O_2$ [M+H]$^+$ requires 339.3748, found 339.3753. Anal. $C_{19}H_{21}F_3O_2$ requires C: 67.44, H: 6.26, found C: 67.51, H, 6.27.

Para-(2,4-trifluoromethylphenyl)-propofol:

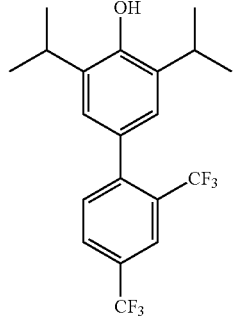 [SMILES: CC(C)c1cc(-c2ccc(C(F)(F)F)cc2C(F)(F)F)cc(C(C)C)c1O]

4-Bromopropofol (300 mg, 1.12 mmol), 2,4-trifluoromethylphenyl boronic acid and tetrakis (triphenylphosphine)

palladium (0) were reacted according to general procedure A to give product as a pale yellow solid (250 mg, 57%). $^1$H NMR δ7.2 (m, 1H), 7.65-7.5 (m, 2H), 7.34-7.15 (m, 3H) 4.85 (s, 1H), 3.25 (m, 2H), 1.2 ppm (d, J=6.85, 12H). $^{13}$C NMR δ148.41, 139.52, 132.78, 130.35, 129.03, 128.39, 127.21, 124.63, 123.29, 118.14, 25.99, 23.83. $C_{20}H_{20}F_6O$ [M+H]$^+$ requires 391.3729, found 391.3761. Anal. $C_{20}H_{20}F_6O$ requires C: 61.54, H: 5.16, found C: 61.22, H: 5.10.

Para-(2,4-difluorophenyl)-propofol:

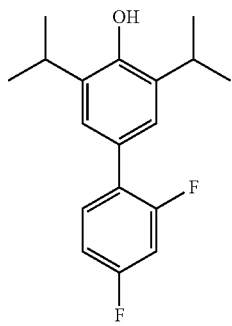

4-Bromopropofol (520 mg, 1.94 mmol), 2,4-difluorophenyl boronic acid and tetrakis (triphenylphosphine) palladium (0) were reacted according to general procedure A to give product as a pale yellow solid (350 mg, 56%). $^1$H NMR δ7.5 (m, 1H), 7.1 (s, 2H), 6.8-6.7 (m, 2H) 4.85 (s, 1H), 3.25 (m, 2H), 1.2 ppm (d, J=6.85, 12H). $^{13}$C NMR δ164.11, 160.35, 147.93, 139.11, 131.15, 129.37, 127.33, 112.06, 105.34, 26.77, 24.11. $C_{18}H_{20}F_2O$ [M+H]$^+$ requires 291.3589, found 291.3565. Anal. $C_{18}H_{20}F_2O$ requires C: 74.46, H: 6.94, found C: 74.51, H: 6.99.

Para-(2-chlorophenyl)-propofol:

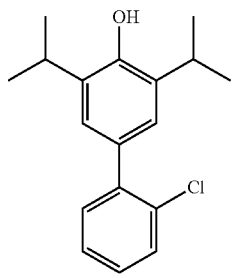 [SMILES: CC(C)c1cc(-c2ccccc2Cl)cc(C(C)C)c1O]

4-Bromopropofol (300 mg, 1.12 mmol), 2-chlorophenyl boronic acid and tetrakis (triphenylphosphine) palladium (0) were reacted according to general procedure A to give product as a pale yellow oil (195 mg, 60%). $^1$H NMR δ7.4-7.1 (m, 6H), 4.85 (s, 1H), 3.25 (m, 2H), 1.2 ppm (d, J=6.85, 12H). $^{13}$C NMR δ146.93, 139.31, 137.43, 133.10, 129.29, 125.93, 26.74, 23.71. HRMS: (EI)$^-$ $C_{18}H_{20}OCl$ [M+H]$^-$ requires 287.1203, found 287.1216. Anal. $C_{18}H_{20}OCl$ requires C: 74.86, H, 7.33, found C: 74.90, H: 7.33.

Compound Testing

Comparative Ethanol Solubility Assay

The solubility in ethanol of a series of para-substituted propofol analogues was determined visually using 5 mg compound/1 ml of ethanol. A small number of the analogues tested were not in accordance with the present invention, but are included below for comparative purposes with the large number of analogues tested that were in accordance with the present invention. All compounds tested were soluble except where stated below.

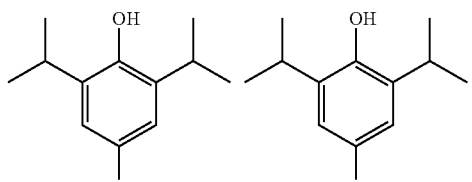

Molecular Weight: 257.17
MJ-2-01 575 mg

Molecular Weight: 223.27
MJ-2-02 100 mg

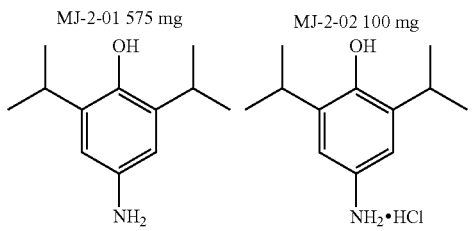

Molecular Weight: 193.29
MJ-2-04 100 mg

Molecular Weight: 229.75
MJ-2-05 100 mg

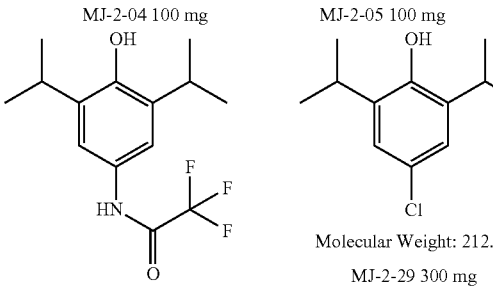

Molecular Weight: 289.29
MJ-2-28 205 mg
Insoluble

Molecular Weight: 212.72
MJ-2-29 300 mg

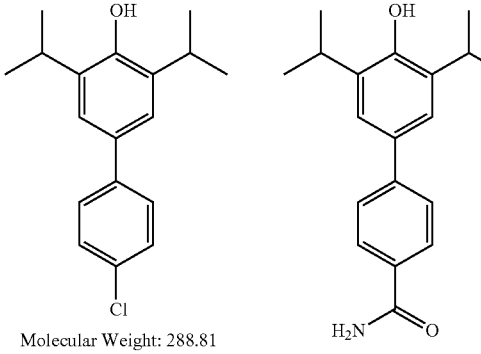

Molecular Weight: 288.81
MJ-2-11 120 mg

Molecular Weight: 297.39
MJ-2-09 212 mg

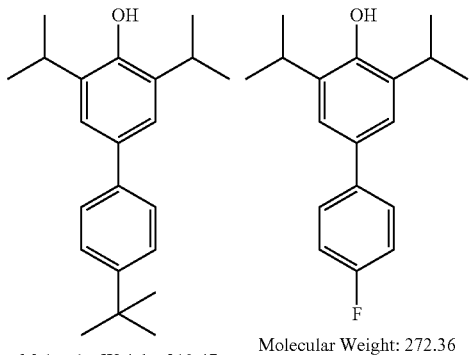

Molecular Weight: 310.47
MJ-2-08 400 mg
Insoluble

Molecular Weight: 272.36
MJ-2-21 210 mg

-continued

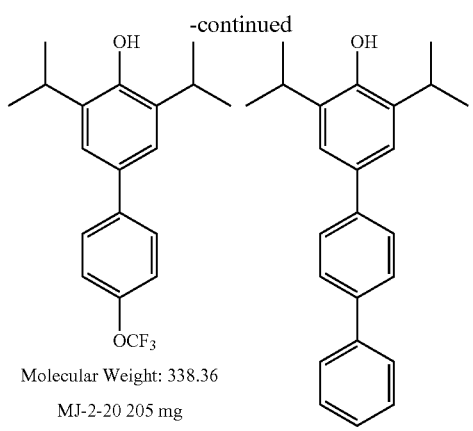

Molecular Weight: 338.36
MJ-2-20 205 mg

MJ-2-37 100 mg
Insoluble

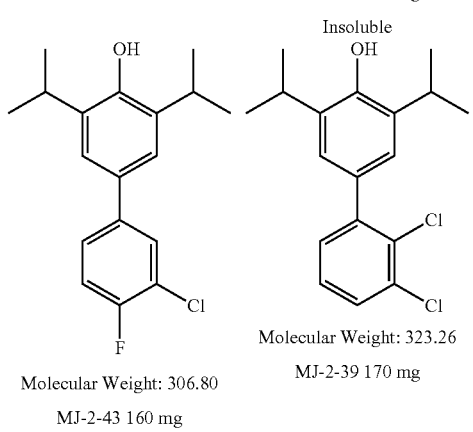

Molecular Weight: 306.80
MJ-2-43 160 mg

Molecular Weight: 323.26
MJ-2-39 170 mg

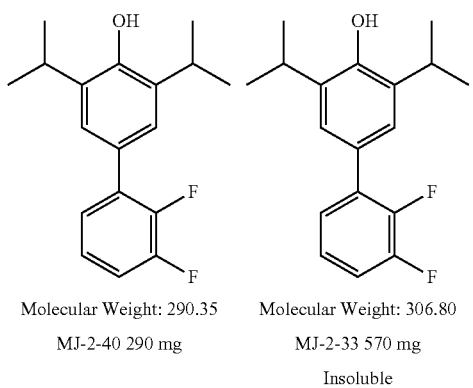

Molecular Weight: 290.35
MJ-2-40 290 mg

Molecular Weight: 306.80
MJ-2-33 570 mg
Insoluble

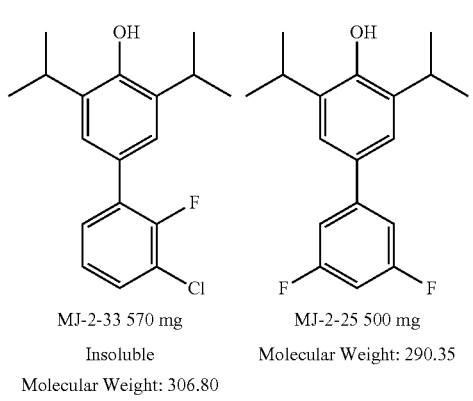

MJ-2-33 570 mg
Insoluble
Molecular Weight: 306.80

MJ-2-25 500 mg
Molecular Weight: 290.35

-continued

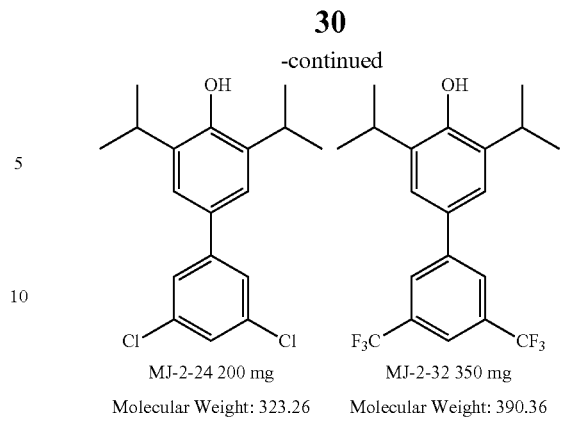

MJ-2-24 200 mg
Molecular Weight: 323.26

MJ-2-32 350 mg
Molecular Weight: 390.36

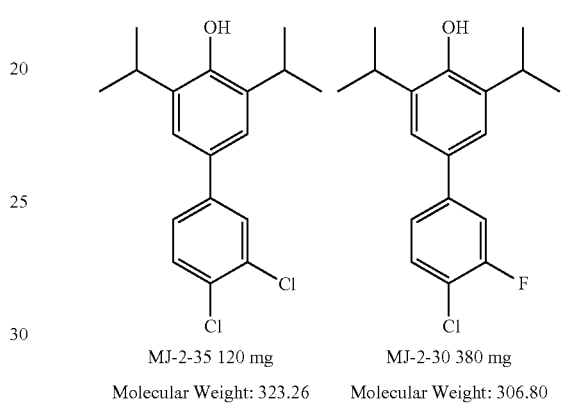

MJ-2-35 120 mg
Molecular Weight: 323.26

MJ-2-30 380 mg
Molecular Weight: 306.80

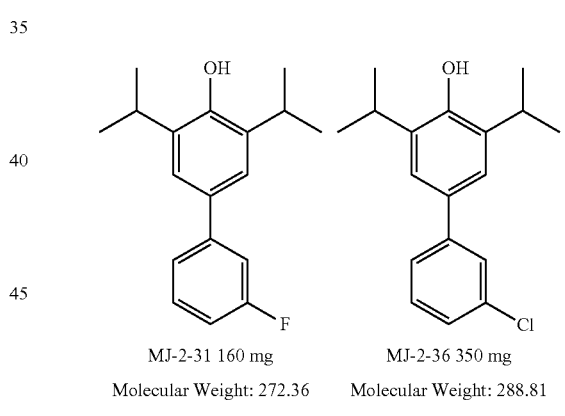

MJ-2-31 160 mg
Molecular Weight: 272.36

MJ-2-36 350 mg
Molecular Weight: 288.81

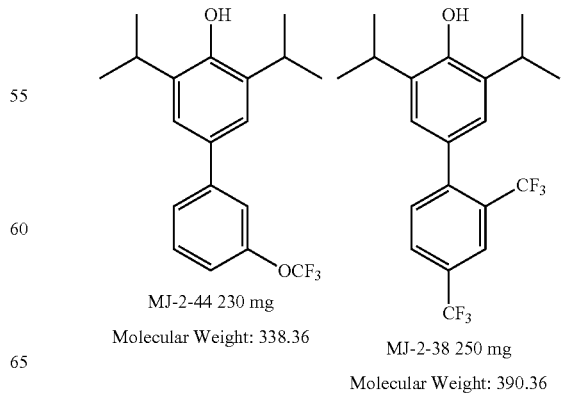

MJ-2-44 230 mg
Molecular Weight: 338.36

MJ-2-38 250 mg
Molecular Weight: 390.36

-continued

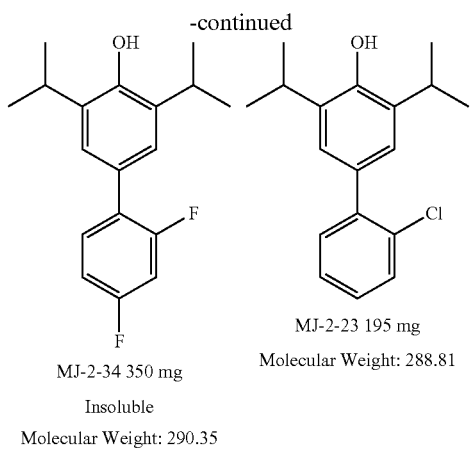

MJ-2-34 350 mg
Insoluble
Molecular Weight: 290.35

MJ-2-23 195 mg
Molecular Weight: 288.81

Determination of Compound Potency

Preliminary experiments were conducted, as described below, to investigate the effect of a representative sample of propofol analogues according to the present invention on Glycine receptor activation and chloride currents. A skilled person will appreciate that these data suggest that the analogues are suitable for use as analgesics.

Methods

Cell Culture, Transfection

Rat $\alpha_1$ glycine receptor subunits were transiently transfected into transformed human embryonic kidney cells (HEK 293). $\alpha_1$ glycine receptor subunits efficiently form homomeric receptors in heterologous expression systems. Cells were cultured in Dulbecco's modified Eagle's medium (DMEM, Biochrom, Berlin, Germany), supplemented with 10% fetal calf serum (FCS, Biochrom, Berlin, Germany), 100 U ml$^{-1}$ penicillin and 100 µg ml$^{-1}$ streptomycin at 37° C. in a 5% $CO_2$/air incubator. For transfection, cells were suspended in a buffer containing 50 mM $K_2HPO_4$ and 20 mM K-acetate, pH 7.35. For co-transfection of rat $\alpha_1$ glycine receptor subunits, the corresponding cDNA, each subcloned in the pCIS2 expression vector (Invitrogen, San Diego, USA), was added to the suspension. To visualize transfected cells, they were co-transfected with cDNA of green fluorescent protein (GFP 10 µg ml$^{-1}$). For transfection, we used an electroporation device by EquiBio (Kent, UK). Transfected cells were replated on glass-coverslips and incubated for 15 to 24 hours before recording.

Chemicals & Solutions

All chemicals were from Sigma Chemicals (Deisenhofen, Germany), unless otherwise noted.

The compounds according to the present invention under investigation were prepared as 1 M stock solution in ethanol, light-protected and stored in glass vessels at −20° C. Concentrations were calculated from the amount injected into the glass vials. Drug-containing vials were vigorously vortexed for 60 min. Glycine and picrotoxin were dissolved directly in bath solution.

Patch electrodes contained [mM] KCl 140, $MgCl_2$ 2, EGTA 11, HEPES 10, glucose 10; the bath solution contained [mM] NaCl 162, KCl 5.3, $NaHPO_4$ 0.6, $KH_2PO_4$ 0.22, HEPES 15, glucose 5.6.

Experimental Set-Up

Standard whole-cell experiments (Hamill et al., (1981) Pflügers Arch., 391, 85-100.) were performed at −30 mV membrane potential. A tight electrical seal of several GΩ formed between the cell membrane and a patch-clamp electrode allows inward currents due to agonist-induced channel activation to resolve in the pA range. Electrical resistance of the pipettes was around 5 MΩ, corresponding to a total access resistance in the whole-cell configuration of about 10 MΩ. The compounds according to the present invention under investigation were applied to the cells via a smooth liquid filament achieved with a single outflow (glass tubing 0.15 mm inner diameter) connected to a piezo crystal. The cells were placed at the interface between this filament and the continuously flowing background solution. When a voltage pulse was applied to the piezo, the tube was moved up and down onto or away from the cell under investigation. Correct positioning of the cell in respect to the liquid filament was ensured applying a saturating (1000 µM) glycine pulse before and after each test experiment. Care was taken to ensure that the amplitude and the shape of the glycine-activated current had stabilized before proceeding with the experiment. Test solution and glycine (1000 µM) were applied via the same glass-polytetrafluoroethylen perfusion system, but from separate reservoirs. The contents of these reservoirs were mixed at a junction immediately before entering the superfusion chamber.

The compounds under test were applied alone in order to determine their direct agonistic effects. A new cell was used for each compound and each protocol, at least three different experiments were performed for each setting. The amount of the diluent ethanol corresponding to the highest compound concentration used was 34 000 µM. We have previously shown that the ethanol itself has no effect at this concentration on direct activation.

Current Recording and Analysis

For data acquisition and further analysis the inventors used the Axopatch 200B amplifier in combination with pClamp6 software (Axon Instruments, Union City, Calif., USA). Currents were filtered at 2 kHz. Fitting procedures were performed using a non-linear least-squares Marquardt-Levenberg algorithm. Details are provided in the appropriate figure legends or in the results section.

Activated currents were normalized to their own maximum response. The dose-response-curves were fitted according to $(I_{norm}=[1+(EC_{50}/[C])^{n_H}]^{-1})$, where $I_{norm}$ is the current induced directly by the respective concentration [C] of the compound, normalized to the maximum inward current. $EC_{50}$ is the concentration required to evoke a response amounting to 50% of their own maximal response and $n_H$ is the Hill coefficient.

Results

Initial $EC_{50}$ values and Hill-coefficients (±SD) derived from fits of the Hill equation to the normalized response in $\alpha_1$ receptors are depicted in FIGS. 1, 2 and 3 and listed in Table 1 below.

TABLE 1

$EC_{50}$ values and Hill coefficients (+s.d.) derived from fits of the Hill equation to the normalised coactivating response (with respect to the effect of the highest concentration tested) in $\alpha_1$ receptors.

| | $\alpha_1$ homomer | |
|---|---|---|
| | $EC_{50}$ (nM) | $n_H$ |
| 4-(p-tert-butylphenyl)-propofol (FIG. 1) | 0.05 ± 0.03 | 2.0 ± 0.4 |
| 4-(p-chlorophenyl)-propofol (FIG. 2) | 0.2 ± 0.3 | 1.1 ± 0.5 |
| 4-trifluoroacetamide-propofol | 0.3 | — |
| 4-(m-fluoro-p-chlorophenyl)-propofol | 0.8 | — |
| 4-(p-biphenyl)-propofol (FIG. 3) | 0.8 ± 0.2 | 2.6 ± 1.2 |

As can be seen from Table 1 all of the analogues tested exhibited significant potency in the nanomolar range.

A further series of tests to determine $EC_{50}$ values for the five compounds shown in Table 1 above indicated that two of the compounds exhibited even lower potency than was observed in the initial tests. In the later tests, 4-trifluoroacetamide-propofol exhibited an $EC_{50}$ of 0.11 nM and 4-(m-fluoro-p-chlorophenyl)-propofol exhibited an $EC_{50}$ of 0.07 nM.

Conclusions

In the preceding Examples a library of aryl-substituted propofol analogues were prepared in high yield from 4-bromo-propofol in a one-step Suzuki reaction. This proved that the 4-halo atom in 4-halo propofol can readily be replaced with an aromatic ring. From initial screening data it appeared that analogues of this nature had nanomolar or even, in some cases, sub-nanomolar activity. A further interesting observation was that a 4-biphenyl group was also tolerated. While the inventors do not wish to be bound by any particular theory, this observation, together with the structure-activity relationship (SAR) data obtained to date, would seem to support the presence of a hydrophobic channel within which the lipophilic/biphenyl residues can bind.

Plasma Kinetics of Three Propofol Derivatives in Rat In Vivo

1. Summary

The in vivo plasma kinetics of 4-Chloropropofol, 4-(para-Chlorophenyl)-propofol and Para-(3-Fluoro,4-chlorophenyl)-propofol were determined after i.v. and p.o dosing into rat.

The compounds show generally high clearance values but half lifes are prolonged by large volumes of distribution. 4-Chloropropofol and Para-(3-Fluoro,4-chlorophenyl)-propofol are observed in plasma after oral administration. Peak plasma concentration is reached rapidly but terminal half life is increased considerably compared to i.v. dosing. Therefore, there is certain amount of uncertainty in the bioavailability estimates.

2. Materials and Methods 2.1 Chemicals, Biological Materials and Incubations 2.1.1 Chemicals HPLC grade methanol and acetonitrile were obtained from Merck (Darmstadt, Germany). Ammonium acetate, ammonium formate, acetic acid and formic acid were obtained from BDH Laboratory Supplies (Poole, UK). Other chemicals were obtained mainly from Sigma Chemical Company (St. Louis, Mo., USA) and Boehringer (Ingelheim, Germany) and were of the highest purity available. Water was in-house freshly prepared with Milli-Q (Millipore ay, Espoo, Finland) purification system and UP grade (ultra pure, 18.2 MQ).

2.1.2 Animal Experiments and Samples

The test substances, 4-Chloropropofol, CK-2-3 and CK-2-9 were dosed at 20 mg/kg p.o and 2 mg/kg i.v. into the rat. Whole blood samples were taken from a lateral tail vein for plasma separation at time points 0 min, 30 min, 1 h, 2 h and 4 h after p.o. dosing; and 0 min, 15 min, 30 min, 1 h, and 2 h after i.v. dosing, while the terminal samples at time point 6 h after dosing (p.o and Lv.) were taken by cardiac puncture. All time points were taken from a single rat, and all experiments were carried out in triplicate.

2.1.3 Sample Preparation

The samples were thawn at room temperature and prepared by protein precipitation with ratio 1:2 of plasma and acetonitrile and were centrifuged 10 minutes at 16 100×g (Eppendorf 5415D, Eppendorf AG, Hamburg, Germany) before injection to UPLCIMSMS system. The standard samples were prepared similarly, after spiking blank plasma samples to 0.5, 2, 5, 10, 20, 50, 200, 500, 1000 and 2000 ng/ml of the analyte compounds.

2.1.4 Calculations

The pharmacokinetic parameters for study compounds were calculated by WinNonlin Pro (Pharsight Corp, CA) using standard noncompartmental methods. The volume of distribution ($V_d$) was based on the terminal phase. The elimination phase half-life ($t_{1/2}$) was calculated by least-squares regression analysis of the terminal linear part of the log concentration-time curve. The area under the plasma concentration-time curve (AUC) was determined by use of the linear trapezoidal rule up to the last measurable concentration and thereafter by extrapolation of the terminal elimination phase to infinity. The area under the plasma concentration-time curve without terminal extrapolation is reported as AUC 0-6 h. The mean residence time (MRT) representing the average amount of time a compound remains in a compartment or system was calculated extrapolating the drug concentration profile to infinity. The maximum plasma concentration ($c_{max}$) and the time to $c_{max}$ ($t_{max}$) were derived directly from the plasma concentration data. The tentative oral bioavailability (F) was calculated by dividing the AUC after p.o. administration by the AUC after i.v. administration taking into account the differences in dose, i.e. F=AUC(p.o.)/Dose(p.o.)/AUC (i.v)/Dose (p.o), and reported as percentages (%).

2.2 Analytical Methods 2.2.1 Liquid Chromatography-Mass Spectrometry

A Waters Acquity chromatographic system (Waters Corp., Milford, Mass., USA) with autosampler, vacuum degasser and column oven was used. The analytical column used for all compounds was a Waters BEH ShieldRP18, (2.1×50 mm, 1.7 μm, Waters Corp, Milford, Mass., USA) together with an on-line filter. The eluents were 0.1% acetic acid (A, pH 3.2) and acetonitrile (B). A linear gradient elution from 5% B to 35% B in 0-2 minutes, from 35% B to 85% B in 2.0-3.0 min was employed, followed by 1 min isocratic elution with 805% B and column equilibration. The flow rate was 0.5 ml/min and the column oven temperature was 35° C. LC/MS/MS/data was acquired with a Micromass Quattro Premier triple quadrupole mass spectrometer equipped with a LockSpray electrospray ionization source. A negative ion mode ionisation was used. The multiple reaction monitoring (MRM) mode of detection was used. The mass spectrometer and UPLC system were operated under Micromass MassLynx 4.1 software. Complete LC/MS/MS parameters are presented in Appendix I.

3. Results and Conclusions 3.1 Quantitative Analyses

The performance ("on-the-fly validation") of the analytical method is shown in FIG. 7. Examples of the LC/MS/MS chromatograms are shown in the FIG. 7.

Detection/quantitation limits between 2 ng/ml and 10 ng/ml in plasma were obtained for each compound. Calibration curves for quantification were generated by fitting the ratio of the external standard peak areas as a function of the concentration, excluding the point of origin and using 1/x weighting and linear or quadratic fitting. The ranges up to 2000 ng/ml were fitted for calibration curves. The backcalculated accuracies (n=2) within quantification ranges were between 82-119% at quantitation limit and higher concentrations. The overall precisions 12.0-17.0% were calculated from the standard samples (two injection/concentration), using Snedecor equation $S=(\Sigma d^2/2n)^{0.5}$, in which S=precision, d is the difference between duplicates expressed as % of the mean value, and N is the number of standard concentration. The concentrations of each study compound in the samples are shown in the Appendices IV-VI.

3.2 Pharmacokinetics

Figure 6:
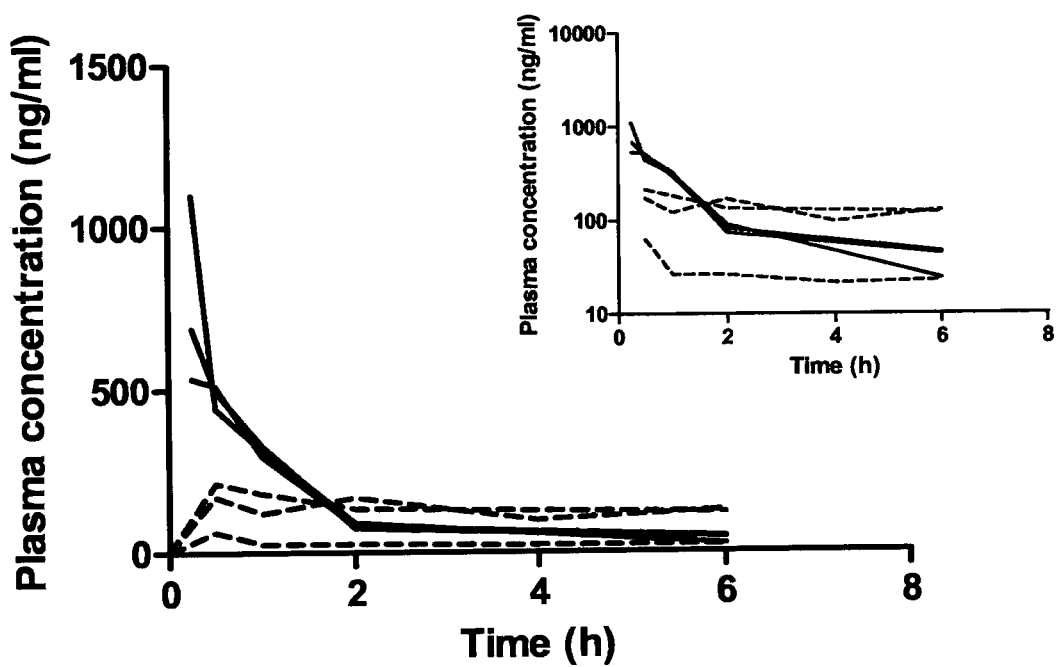

Pharmacokinetic parameters for the study compounds are summarized in Table 2 below and parameters of individual animals are shown in Tables 3-5 below. The study compound plasma concentration vs. time curves are represented in FIGS. 4-6.

All compounds showed plasma kinetic profiles with evidence of initial distribution and final elimination phases.

4-Chloropropofol had very high clearance value in comparison to rat liver blood flow (55.2 ml/min, Davies, B and Morris, T, (1993). Physiological parameters in laboratory animals and humans. Pharm Res 10: 1093-5). Despite high clearance the half life is intermediate because of high volume of distribution. Oral bioavailability is good (F=72.4%) and absorption is rapid ($T_{max}$=30 min). Since drug clearance is rapid, the apparently limited first-pass extraction may originate from saturation of liver metabolism because of high drug concentration in portal vein after rapid absorbtion. Clearance is similar to i.v. dosing but half life is considerably increased. Pharmacokinetic analysis suggests that the increase in volume of distribution is the reason for this but the mechanism behind this is not clear. The ADC calculation may be somewhat skewed by the long terminal half life that can be absorption rate limited (illustrated by the difference in ADC and ADC 0-6 h values after p.o. administration). Therefore, the tentative bioavailability should be considered as a maximum value.

4-(para-Chlorophenyl)-propofol was detected in plasma only after i.v. administration. The clearance was in the range of hepatic blood flow and half life about 1.5 hours. Volume of distribution was quite large (>6 liters/kg). The reason for low bioavailability may be poor absorption or extensive first pass metabolism.

Para-(3-Fluoro,4-chlorophenyl)-propofol showed intermediate clearance and half life after i.v. dosing. The tentative oral bioavailability was about 18%. The clearance is similar to i.v. clearance but the volume of distribution is much higher than after i.v. dosing. The behaviour leads to similar conclusions as for 4-Chloropropofol. The ADC calculation may be somewhat skewed by the long terminal half life that can be absorption rate limited (illustrated by the difference in ADC and ADC 0-6 h values after p.o. administration). Therefore, the tentative bioavailability should be considered as a maximum value.

TABLE 2

Pharmacokinetic parameters of the study compounds after p.o and i.v. administrations (n = 3).

| Compound | Parameter | | i.v Mean | i.v SE | p.o. Mean | p.o. SE | F (%) |
|---|---|---|---|---|---|---|---|
| | | | 1 mg/kg* | | 8 mg/kg* | | |
| 4-Cl-propofol | ADC | min * µg/mL | 7.39 | 1.68 | 42.8 | 8.78 | 72.4 |
| | ADC 0-6 h | min * µg/mL | 6.29 | 3.18 | 18.7 | 5.8 | |
| | $c_{max}$ | µg/mL | 0.11 | 0.03 | 0.1 | 0.02 | |
| | $t_{max}$ | min | 15 | 0 | 30 | 0 | |
| | $t_{1/2}$ | min | 48.8 | 19.9 | 398 | 96.4 | |
| | CL/F | mL/min/kg | 148 | 27.8 | 201 | 34.3 | |
| | CL | mL/min/kg | 148 | 27.8 | 146 | 24.8 | |
| | Vd/F | L/kg | 11.8 | 5.64 | 110 | 27.4 | |
| | Vd | L/kg | 11.8 | 5.64 | 79.6 | 19.8 | |
| | MRT | min | 48.7 | 16 | 609 | 152 | |
| | | | 2 mg/kg | | 20 mg/kg | | |
| 4-(p-Cl—Ph)-propofol | ADC | min * µg/mL | 48.6 | 10.2 | N.D. | N.D. | 0.0 |
| | ADC 0-6 h | min * µg/mL | 46.6 | 17.6 | N.D. | N.D. | |
| | $c_{max}$ | µg/mL | 0.55 | 0.12 | N.D. | N.D. | |
| | $t_{max}$ | min | 15 | 0 | N.D. | N.D. | |
| | $t_{1/2}$ | min | 96.8 | 5.01 | N.D. | N.D. | |
| | CL/F | mL/min/kg | 44.4 | 7.87 | N.D. | N.D. | |
| | CL | mL/min/kg | 44.4 | 7.87 | N.D. | N.D. | |
| | Vd/F | L/kg | 6.09 | 0.83 | N.D. | N.D. | |
| | Vd | L/kg | 6.09 | 0.83 | N.D. | N.D. | |
| | MRT | min | 76.3 | 14.7 | N.D. | N.D. | |
| p-(3-F,4-Cl—Ph)-propofol | ADC | min * µg/mL | 69.2 | 5.72 | 123 | 42 | 17.8 |
| | ADC 0-6 h | min * µg/mL | 64.1 | 6.88 | 34.6 | 12.6 | |
| | $c_{max}$ | µg/mL | 0.77 | 0.17 | 0.15 | 0.04 | |
| | $t_{max}$ | min | 15 | 0 | 30 | 0 | |
| | $t_{1/2}$ | min | 91 | 5.01 | 789 | 185 | |
| | CL/F | mL/min/kg | 29.3 | 2.28 | 231 | 103 | |
| | CL | mL/min/kg | 29.3 | 2.28 | 41.1 | 18.3 | |
| | Vd/F | L/kg | 3.87 | 0.5 | 306 | 195 | |
| | Vd | L/kg | 3.87 | 0.5 | 54.4 | 34.7 | |
| | MRT | min | 104 | 19.1 | 1160 | 256 | |

SE = standard error.

*The dosing solutions were analysed due to problems in their preparation. The results showed the actual doses to be about 40% (p.o) and 50% (I.v.) of the aimed doses.

N.D. Compound was not detected in plasma after p.o. administration.

TABLE 3

PK-parameters from individual animals for 4-Cl-propofol

| Parameter | | 1 mg/kg i.v.* | | | 8 mg/kg p.o.* | | |
|---|---|---|---|---|---|---|---|
| | | A4 | A5 | A6 | A1 | A2 | A3 |
| ADC | min * µg/mL | 10.7 | 5.43 | 6.01 | 33.2 | 34.9 | 60.4 |
| $c_{max}$ | µg/mL | 0.17 | 0.07 | 0.09 | 0.12 | 0.05 | 0.12 |
| $t_{max}$ | min | 15 | 15 | 15 | 30 | 30 | 30 |
| $t_{1/2}$ | min | 16.3 | 81.8 | 48.2 | 205 | 493 | 496 |
| CL/F | mL/min/kg | 93.2 | 184 | 166 | 241 | 229 | 133 |
| Vd/F | L/kg | 2.19 | 21.7 | 11.6 | 71.3 | 163 | 94.7 |
| MRT | min | 31.8 | 80.8 | 33.6 | 305 | 760 | 764 |

*The dosing solutions were analysed due to problems in their preparation. The results showed the actual doses to be about 40% (p.o) and 50% (i.v.) of the aimed doses

TABLE 4

PK-parameters from individual animals for 4-(p-Cl—Ph)-propofol

| Parameter | | 2 mg/kg i.v. | | | 20 mg/kg p.o. | | |
|---|---|---|---|---|---|---|---|
| | | A7 | A8 | A9 | A10 | A11 | A12 |
| ADC | min * µg/mL | 36.3 | 40.8 | 68.8 | N.D. | N.D. | N.D. |
| $c_{max}$ | µg/mL | 0.4 | 0.46 | 0.78 | N.D. | N.D. | N.D. |
| $t_{max}$ | min | 15 | 15 | 15 | N.D. | N.D. | N.D. |
| $t_{1/2}$ | min | 91.2 | 92.4 | 107 | N.D. | N.D. | N.D. |
| CL/F | mL/min/kg | 55.1 | 49.1 | 29.1 | N.D. | N.D. | N.D. |
| Vd/F | L/kg | 7.26 | 6.54 | 4.48 | N.D. | N.D. | N.D. |
| MRT | min | 91.4 | 90.5 | 46.9 | N.D. | N.D. | N.D. |

N.D. Compound was not detected in plasma after p.o. administration

TABLE 5

PK-parameters from individual animals for p-(3-F,4-Cl—Ph)-propofol

| Parameter | | 2 mg/kg i.v. | | | 20 mg/kg p.o. | | |
|---|---|---|---|---|---|---|---|
| | | A16 | A17 | A18 | A13 | A14 | A15 |
| ADC | min * µg/mL | 80.4 | 65.7 | 61.6 | 131 | 46.1 | 191.0 |
| $c_{max}$ | µg/mL | 1.1 | 0.69 | 0.54 | 0.21 | 0.06 | 0.17 |
| $t_{max}$ | min | 15 | 15 | 15 | 30 | 30 | 30 |
| $t_{1/2}$ | min | 81.8 | 92 | 99.1 | 468 | 1110 | 788 |
| CL/F | mL/min/kg | 24.9 | 30.4 | 32.5 | 153 | 434 | 105 |
| Vd/F | L/kg | 2.94 | 4.04 | 4.64 | 103 | 695 | 119 |
| MRT | min | 67.5 | 114 | 131 | 710 | 1590 | 1180 |

Appendices

APPENDIX I

LC/MS-MS parameters in analyses

Waters Acquity UPLC + Waters Quattro Premier triple quadrupole mass spectrometer
Waters Acquity BEH ShieldRP18 (2.1 × 50 mm, 1.8 µm) column with quard filter

| | |
|---|---|
| Desolvatation Gas Flow (L/h) | 800 |
| Capillary (V) | 2500 |
| Desolvation Temp (° C.) | 350 |
| Source Temp (° C.) | 150 |
| CID pressure (mbar) | $3.8 \times 10^{-3}$ |

APPENDIX I-continued

LC/MS-MS parameters in analyses

MRM transition reactions for each compound:

| Compound | MRM reaction | Collision energy (eV) | Cone voltage (V) | Retention time (min) | Polarity |
|---|---|---|---|---|---|
| CK-1-1 | m/z 211 > 196 | 18 | 48 | 3.35 | ESI− |
| CK-2-3 | m/z 287 > 236 | 28 | 48 | 3.56 | ESI− |
| CK-2-9 | m/z 305 > 254 | 28 | 48 | 3.59 | ESI− |

Gradient
Eluent A = 0.1% acetic acid (pH 3.2), B = acetonitrile

| Time | flow | A % | B % | curve |
|---|---|---|---|---|
| 0.00 | 0.500 | 95.0 | 5.0 | 6 |
| 2.00 | 0.500 | 65.0 | 35.0 | 6 |
| 3.00 | 0.500 | 15.0 | 85.0 | 6 |
| 4.00 | 0.500 | 15.0 | 85.0 | 6 |
| 4.10 | 0.500 | 95.0 | 5.0 | 6 |
| 6.00 | 0.500 | 95.0 | 5.0 | 6 |

APPENDIX III

Performance of the analytical method

| | Accuracies, %, n = 2 | | |
|---|---|---|---|
| | 4-Cl-propofol | 4-(p-Cl—Ph)-propofol | p-(3-F,4-Cl—Ph)-propofol |
| std 0.5 ng/ml | — | — | — |
| std 1 ng/ml | — | — | — |
| std 2 ng/ml | — | — | 82.3 (LoD/LoQ) |
| std 5 ng/ml | 44.9 (LoD) | — | 100.3 |
| std 10 ng/ml | 102.7 (LoQ) | 93.1 (LoD/LoQ) | 94.3 |
| std 20 ng/ml | 119.2 | 116.2 | 100.4 |
| std 50 ng/ml | 115.1 | 121.1 | 114.2 |
| std 100 ng/ml | 114.7 | 125.0 | 108.4 |
| std 200 ng/ml | 106.0 | 89.8 | 90.4 |
| std 500 ng/ml | 99.1 | 95.3 | — |
| std 1000 ng/ml | 95.7 | 100.7 | 93.9 |
| std 2000 ng/ml | 93.2 | 99.6 | 93.1 |
| Snedecor-precision | 14.4% | 17.0% | 12.0% |
| R2 of the calibration curve | 0.991 | 0.962 | 0.991 |

LoD = limit of detection
LoQ = limit of quantification

APPENDIX IV

Concentrations of 4-Cl-propofol in the samples

| sample | ng/ml in plasma |
|---|---|
| G1 A1 CK1-1 po 0 min | — |
| G1 A2 CK1-1 po 0 min | — |
| G1 A3 CK1-1 po 0 min | — |
| G1 A1 CK1-1 po 30 min | 116 |
| G1 A2 CK1-1 po 30 min | 51.0 |
| G1 A3 CK1-1 po 30 min | 121 |
| G1 A1 CK1-1 po 1 h | 99.8 |
| G1 A2 CK1-1 po 1 h | 47.3 |
| G1 A3 CK1-1 po 1 h | 57.2 |
| G1 A1 CK1-1 po 2 h | 64.3 |
| G1 A2 CK1-1 po 2 h | 25.3 |
| G1 A3 CK1-1 po 2 h | 52.3 |
| G1 A1 CK1-1 po 4 h | 61.8 |
| G1 A2 CK1-1 po 4 h | 36.1 |
| G1 A3 CK1-1 po 4 h | 55.1 |
| G1 A1 CK1-1 po 6 h | 33.8 |
| G1 A2 CK1-1 po 6 h | 32.0 |
| G1 A3 CK1-1 po 6 h | 55.3 |

APPENDIX IV-continued

Concentrations of 4-Cl-propofol in the samples

| sample | ng/ml in plasma |
| --- | --- |
| G2 A4 CK1-1 iv 0 min | — |
| G2 A5 CK1-1 iv 0 min | — |
| G2 A6 CK1-1 iv 0 min | — |
| G2 A4 CK1-1 iv 15 min | 172 |
| G2 A5 CK1-1 iv 15 min | 70.0 |
| G2 A6 CK1-1 iv 15 min | 94.3 |
| G2 A4 CK1-1 iv 30 min | 47.3 |
| G2 A5 CK1-1 iv 30 min | 26.1 |
| G2 A6 CK1-1 iv 30 min | 25.4 |
| G2 A4 CK1-1 iv 1 h | 13.2 |
| G2 A5 CK1-1 iv 1 h | 15.2 |
| G2 A6 CK1-1 iv 1 h | 16.5 |
| G2 A4 CK1-1 iv 2 h | 33.7 |
| G2 A5 CK1-1 iv 2 h | 11.5 |
| G2 A6 CK1-1 iv 2 h | — |
| G2 A4 CK1-1 iv 6 h | — |
| G2 A5 CK1-1 iv 6 h | — |
| G2 A6 CK1-1 iv 6 h | — |

G = group, A = animal

APPENDIX V

Concentrations of 4-(p-Cl—Ph)-propofol in the samples

| sample | ng/ml in plasma |
| --- | --- |
| G3 A7 CK2-3 po 0 min | — |
| G3 A8 CK2-3 po 0 min | — |
| G3 A9 CK2-3 po 0 min | — |
| G3 A7 CK2-3 po 30 min | — |
| G3 A8 CK2-3 po 30 min | — |
| G3 A9 CK2-3 po 30 min | — |
| G3 A7 CK2-3 po 1 h | — |
| G3 A8 CK2-3 po 1 h | — |
| G3 A9 CK2-3 po 1 h | — |
| G3 A7 CK2-3 po 2 h | — |
| G3 A8 CK2-3 po 2 h | — |
| G3 A9 CK2-3 po 2 h | — |
| G3 A7 CK2-3 po 4 h | — |
| G3 A8 CK2-3 po 4 h | — |
| G3 A9 CK2-3 po 4 h | — |
| G3 A7 CK2-3 po 6 h | — |
| G3 A8 CK2-3 po 6 h | — |
| G3 A9 CK2-3 po 6 h | — |
| G4 A110 CK2-3 iv 0 min | — |
| G4 A11 CK2-3 iv 0 min | — |
| G4 A12 CK2-3 iv 0 min | — |
| G4 A110 CK2-3 iv 15 min | 784 |
| G4 A11 CK2-3 iv 15 min | 398 |
| G4 A12 CK2-3 iv 15 min | 456 |
| G4 A110 CK2-3 iv 30 min | 123 |
| G4 A11 CK2-3 iv 30 min | 187 |
| G4 A12 CK2-3 iv 30 min | 307 |
| G4 A110 CK2-3 iv 1 h | 79.7 |
| G4 A11 CK2-3 iv 1 h | 149 |
| G4 A12 CK2-3 iv 1 h | 156 |
| G4 A110 CK2-3 iv 2 h | 63.9 |
| G4 A11 CK2-3 iv 2 h | 62.4 |
| G4 A12 CK2-3 iv 2 h | 74.2 |
| G4 A110 CK2-3 iv 6 h | 13.1 |
| G4 A11 CK2-3 iv 6 h | 14.6 |
| G4 A12 CK2-3 iv 6 h | 14.9 |

G = group, A = animal

APPENDIX VI

Concentrations of p-(3-F,4-Cl—Ph)-propofol in the samples

| sample | ng/ml in plasma |
| --- | --- |
| G5 A13 CK2-9 po 0 min | — |
| G5 A14 CK2-9 po 0 min | — |
| G5 A15 CK2-9 po 0 min | — |
| G5 A13 CK2-9 po 30 min | 213 |
| G5 A14 CK2-9 po 30 min | 63.0 |
| G5 A15 CK2-9 po 30 min | 172 |
| G5 A13 CK2-9 po 1 h | 182 |
| G5 A14 CK2-9 po 1 h | 26.6 |
| G5 A15 CK2-9 po 1 h | 121 |
| G5 A13 CK2-9 po 2 h | 134 |
| G5 A14 CK2-9 po 2 h | 26.2 |
| G5 A15 CK2-9 po 2 h | 168 |
| G5 A13 CK2-9 po 4 h | * |
| G5 A14 CK2-9 po 4 h | 21.5 |
| G5 A15 CK2-9 po 4 h | 97.6 |
| G5 A13 CK2-9 po 6 h | 121 |
| G5 A14 CK2-9 po 6 h | 22.9 |
| G5 A15 CK2-9 po 6 h | 128 |
| 6 A16 CK2-9 iv 0 min | — |
| G6 A17 CK2-9 iv 0 min | — |
| G6 A18 CK2-9 iv 0 min | — |
| G6 A16 CK2-9 iv 15 min | 1100 |
| G6 A17 CK2-9 iv 15 min | 689 |
| G6 A18 CK2-9 iv 15 min | 535 |
| G6 A16 CK2-9 iv 30 min | 444 |
| G6 A17 CK2-9 iv 30 min | 499 |
| G6 A18 CK2-9 iv 30 min | 513 |
| G6 A16 CK2-9 iv 1 h | 316 |
| G6 A17 CK2-9 iv 1 h | 329 |
| G6 A18 CK2-9 iv 1 h | 297 |
| G6 A16 CK2-9 iv 2 h | 90.3 |
| G6 A17 CK2-9 iv 2 h | 74.0 |
| G6 A18 CK2-9 iv 2 h | 81.3 |
| G6 A16 CK2-9 iv 6 h | 24.1 |
| G6 A17 CK2-9 iv 6 h | 44.0 |
| G6 A18 CK2-9 iv 6 h | 46.6 |

G = group, A = animal,
* sample lost in preparation

The invention claimed is:

1. A compound of formula (III)

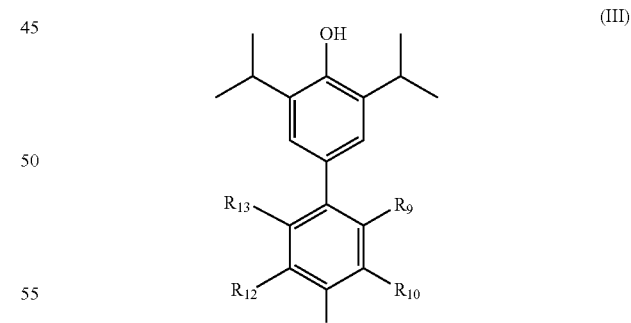

(III)

wherein $R_9$, $R_{10}$, $R_{11}$, $R_{12}$ and $R_{13}$ are each separately selected from the group consisting of hydrogen, halogen, halo-substituted or unsubstituted $C_1$-$C_4$ alkyl, halo-substituted or unsubstituted $C_1$-$C_4$ alkoxy, substituted or unsubstituted amine, substituted or unsubstituted amide, substituted or unsubstituted aryl and substituted or unsubstituted heteroaryl;

or a salt thereof.

2. The compound according to claim 1, wherein at least one of $R_9$ and $R_{13}$ is halogen or halo-substituted or unsubstituted $C_{1-4}$ alkyl.

3. The compound according to claim 2, wherein said halogen is fluorine or chlorine and said alkyl is methyl, ethyl, propyl or butyl.

4. The compound according to claim 1, wherein $R_9$ is selected from the group consisting of fluoro, chloro and trifluoromethyl, and $R_{13}$ is hydrogen.

5. The compound according to claim 1, wherein at least one of $R_{10}$ and $R_{12}$ is selected from the group consisting of hydrogen, halogen and halo-substituted or unsubstituted $C_1$-$C_4$ alkyl.

6. The compound according to claim 5, wherein said halogen is fluorine or chlorine and said alkyl is a halo-substituted $C_{1-4}$ alkyl.

7. The compound according to claim 1, wherein $R_{10}$ is selected from the group consisting of fluoro, chloro, trifluoromethyl and trifluoromethoxy, and $R_{12}$ is selected from the group consisting of hydrogen, fluoro, chloro and trifluoromethyl.

8. The compound according to claim 1, wherein $R_{11}$ is selected from the group consisting of hydrogen, halogen, halo-substituted or unsubstituted $C_1$-$C_4$ alkyl, halo-substituted or unsubstituted $C_1$-$C_4$ alkoxy, and substituted or unsubstituted phenyl.

9. The compound according to claim 8, wherein said halogen is fluorine or chlorine, said alkyl is a halo-substituted $C_{1-4}$ alkyl and said alkoxy is a halo-substituted $C_{1-4}$ alkoxy.

10. The compound according to claim 1, wherein the compound is selected from the group consisting of:

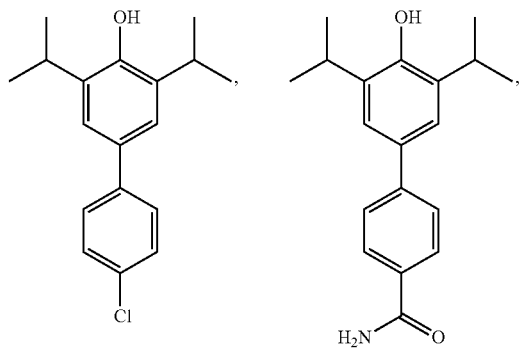

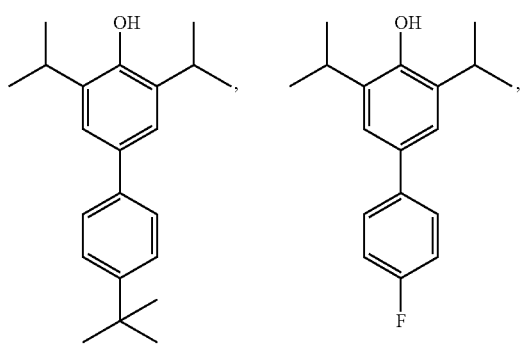

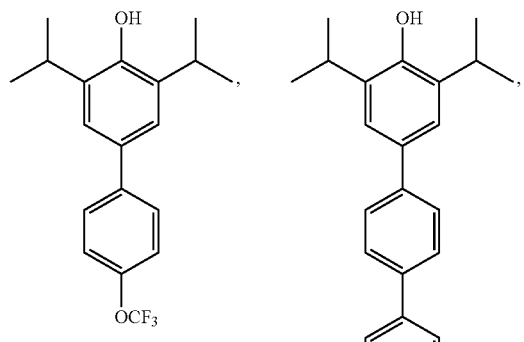

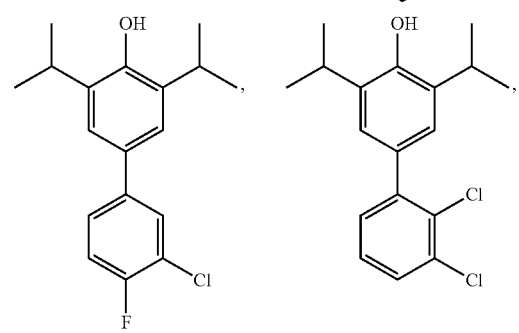

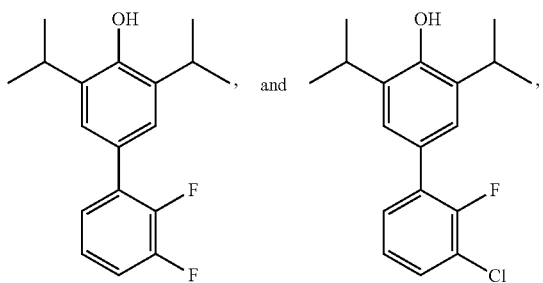 [SMILES: CC(C)c1cc(-c2cccc(F)c2F)cc(C(C)C)c1O ; "," ; "and" ; CC(C)c1cc(-c2cccc(Cl)c2F)cc(C(C)C)c1O ; ","]

or a salt thereof.

11. The compound according to claim 1, wherein the compound is selected from the group consisting of:

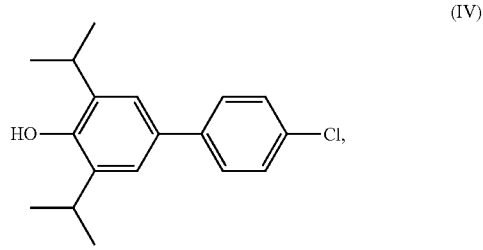
(IV)

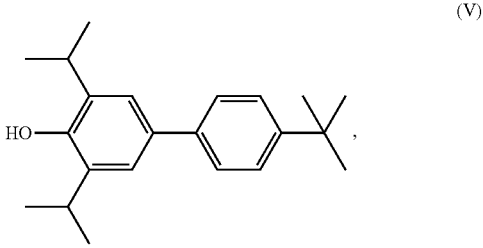
(V)

-continued

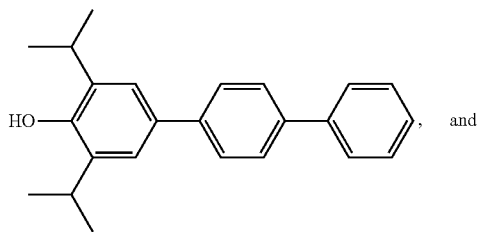
(VI)

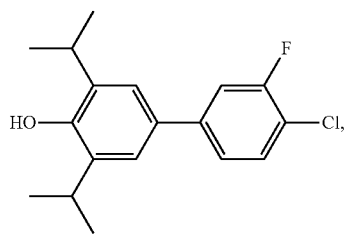
(VII)

or a salt thereof.

12. A pharmaceutical composition comprising a therapeutically effective amount of a compound of formula (III)

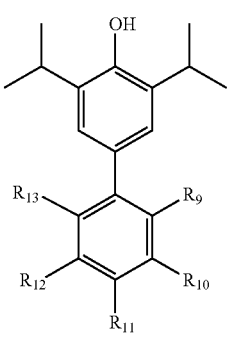
(III)

wherein $R_9$, $R_{10}$, $R_{11}$, $R_{12}$ and $R_{13}$ are each separately selected from the group consisting of hydrogen, halogen, halo-substituted or unsubstituted $C_1$-$C_4$ alkyl, halo-substituted or unsubstituted $C_1$-$C_4$ alkoxy, substituted or unsubstituted amine, substituted or unsubstituted amide, substituted or unsubstituted aryl and substituted or unsubstituted heteroaryl;

or a salt thereof;

and a pharmaceutically acceptable vehicle.

13. The pharmaceutical composition according to claim 12, wherein at least one of $R_9$ and $R_{13}$ is halogen or halo-substituted or unsubstituted $C_{1-4}$ alkyl.

14. The pharmaceutical composition according to claim 12, wherein the compound is selected from the group consisting of:

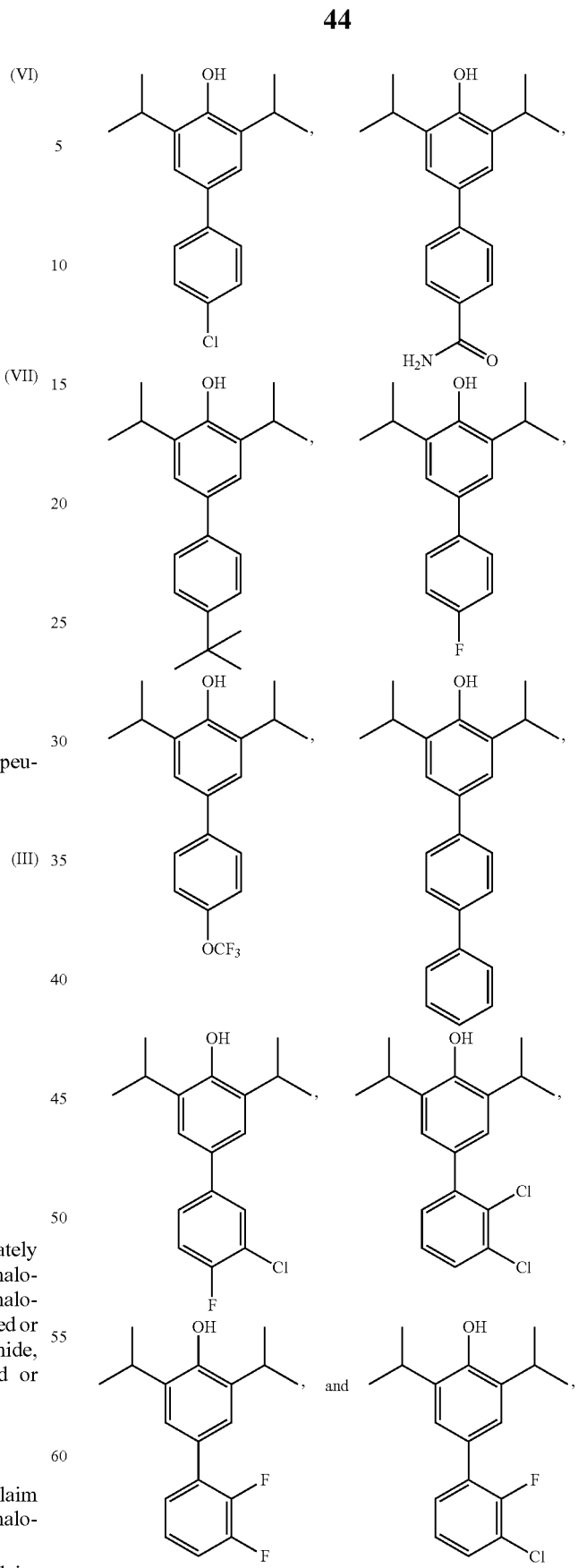

or a salt thereof.

15. The pharmaceutical composition according to claim 12, wherein the compound is selected from the group consisting of:

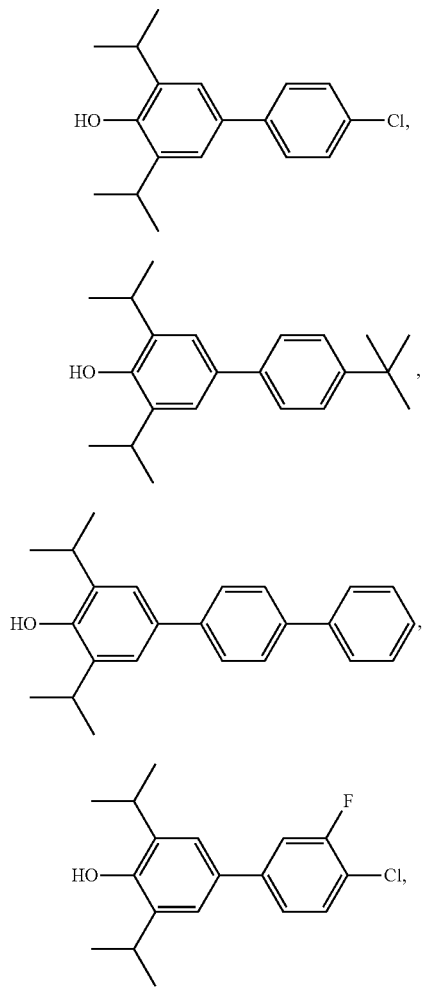

or a salt thereof.

16. A method of treating pain, said method comprising administering to a subject in having pain an effective amount of a compound of formula (III)

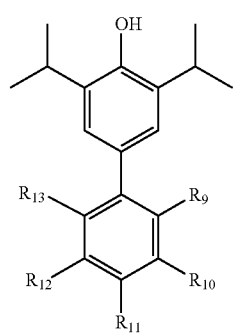

wherein $R_9$, $R_{10}$, $R_{11}$, $R_{12}$ and $R_{13}$ are each separately selected from the group consisting of hydrogen, halogen, substituted or unsubstituted alkyl, substituted or unsubstituted alkoxy, substituted or unsubstituted amine, substituted or unsubstituted amide, substituted or unsubstituted aryl and substituted or unsubstituted heteroaryl;

or a salt thereof.

17. The method according to claim 16, wherein in said compound at least one of $R_9$ and $R_{13}$ is halogen or substituted or unsubstituted $C_{1-4}$ alkyl.

18. The method according to claim 16, wherein the compound is selected from the group consisting of:

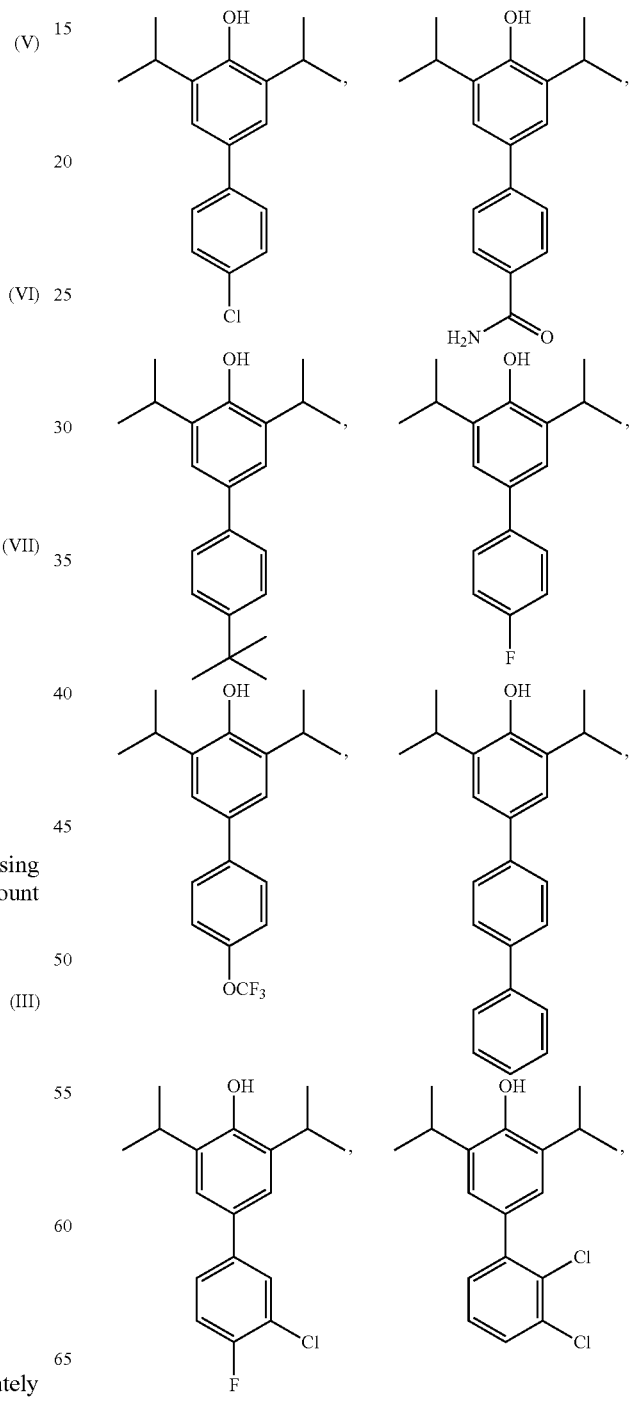

-continued

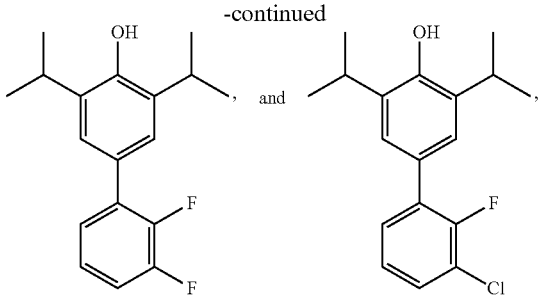

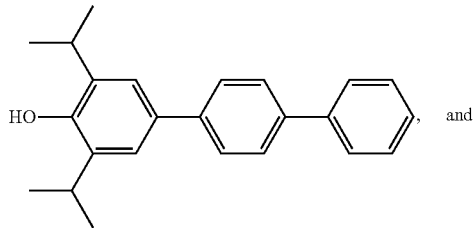 (VI)

or a salt thereof.

19. The method according to claim 16, wherein the compound is selected from the group consisting of:

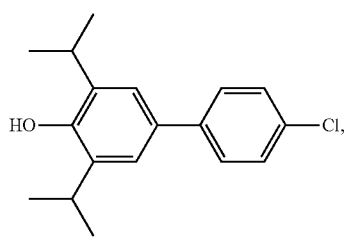 (IV)

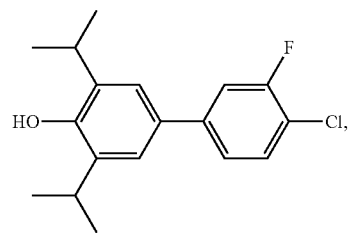 (VII)

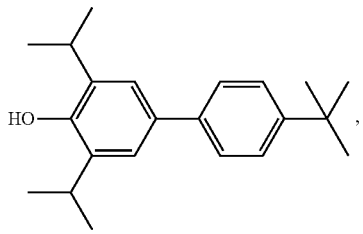 (V)

or a salt thereof.

20. The compound according to claim 1, wherein at least one of $R_{10}$ or $R_{12}$ is hydrogen.

21. The pharmaceutical composition according to claim 12, wherein at least one of $R_{10}$ or $R_{12}$ is hydrogen.

22. The method according to claim 16, wherein at least one of $R_{10}$ or $R_{12}$ is hydrogen.

* * * * *